(12) United States Patent
Woollam et al.

(10) Patent No.: US 7,327,456 B1
(45) Date of Patent: Feb. 5, 2008

(54) SPECTROPHOTOMETER, ELLIPSOMETER, POLARIMETER AND THE LIKE SYSTEMS

(75) Inventors: John A. Woollam, Lincoln, NE (US); Steven E. Green, Lincoln, NE (US); Ping He, Lincoln, NE (US); Blaine D. Johs, Lincoln, NE (US); Craig M. Herzinger, Lincoln, NE (US); Galen L. Pfeiffer, Lincoln, NE (US); Brian D. Guenther, Lincoln, NE (US); Martin M. Liphardt, Lincoln, NE (US); Gerald T. Cooney, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 124 days.

(21) Appl. No.: 11/145,470

(22) Filed: Jun. 6, 2005

Related U.S. Application Data

(63) Continuation-in-part of application No. 10/943,821, filed on Sep. 17, 2004, and a continuation-in-part of application No. 10/376,677, filed on Feb. 28, 2003, now Pat. No. 6,982,792, and a continuation-in-part of application No. 10/178,723, filed on Jun. 24, 2002, now Pat. No. 6,950,182, and a continuation-in-part of application No. 09/864,840, filed on May 24, 2001, now Pat. No. 6,456,376, and a continuation-in-part of application No. 09/854,548, filed on May 14, 2001, now abandoned, and a continuation-in-part of application No. 09/531,877, filed on Mar. 21, 2000, now Pat. No. 6,535,286, and a continuation-in-part of application No. 09/583,229, filed on May 30, 2000, now Pat. No. 6,804,004.

(60) Provisional application No. 60/431,489, filed on Dec. 6, 2002, provisional application No. 60/427,043, filed on Nov. 18, 2002, provisional application No. 60/424,589, filed on Nov. 7, 2002, provisional application No. 60/300,714, filed on Jun. 26, 2001.

(51) Int. Cl.
*G01J 4/00* (2006.01)

(52) U.S. Cl. ....................... 356/364; 356/369
(58) Field of Classification Search ................ 356/364, 356/369; 250/559.9, 225
See application file for complete search history.

(56) References Cited

U.S. PATENT DOCUMENTS

| | | | |
|---|---|---|---|
| 4,210,401 A | 7/1980 | Batten | 356/369 |
| 4,472,633 A | 9/1984 | Motooka | 250/338 |
| 5,045,701 A | 9/1991 | Goldstein et al. | 250/339 |
| 5,373,359 A | 12/1994 | Woollam et al. | 356/328 |
| 5,486,701 A | 1/1996 | Norton et al. | 250/372 |
| 5,582,646 A | 12/1996 | Woollam et al. | 118/708 |
| 5,661,589 A | 8/1997 | Meyer | 359/2.32 |
| 5,706,212 A | 1/1998 | Thompson et al. | 364/525 |
| 5,757,494 A | 5/1998 | Green et al. | 356/369 |
| 5,872,630 A | 2/1999 | Johs et al. | 356/369 |
| 5,929,995 A | 7/1999 | Johs | 356/369 |
| 5,956,145 A | 9/1999 | Green et al. | 356/364 |
| 5,963,327 A * | 10/1999 | He et al. | 356/369 |
| 6,034,777 A | 3/2000 | Johs et al. | 356/369 |
| 6,414,302 B1 | 7/2002 | Freeouf | 250/225 |
| 6,456,376 B1 | 9/2002 | Liphardt et al. | 356/369 |
| 7,136,162 B1 * | 11/2006 | Liphardt et al. | 356/369 |

\* cited by examiner

*Primary Examiner*—Roy M Punnoose
(74) *Attorney, Agent, or Firm*—James D. Welch

(57) ABSTRACT

Disclosed are improvements in ellipsometer and the like systems capable of operating in the Vacuum-Ultra-Violet (VUV) to Near Infrared (NIR) wavelength range, and methodology of use.

9 Claims, 9 Drawing Sheets

SPECTROPHOTOMETER, ELLIPSOMETER, POLARIMETER AND THE LIKE SYSTEMS

This Application is a Continuation-In-Part of Co-Pending Allowed application Ser. No. 10/376,677 Filed Feb. 28, 2003 now U.S. Pat. No. 6,982,792, and of Ser. No. 09/531,877 Filed Mar. 21, 2000 now U.S. Pat. No. 6,535,286; and from 10/178,723 filed Jun. 24, 2002 now U.S. Pat. No. 6,950,182; and 09/583,229 filed May 30, 2000, (now U.S. Pat. No. 6,804,004); and from 09/864,840 filed May 24, 2001, (now U.S. Pat. No. 6,456,376); and 10/943,821 Filed Sep. 17, 2004 and thervia of 09/854,548 filed May 14, 2001 now abandoned; and Claims benefit of Provisional Application Ser. Nos. 60/300,714 filed Jun. 26, 2001, and 60/424,589 filed Nov. 7, 2002, and 60/427,043 filed Nov. 18, 2002 and 60/431,489 filed Dec. 6, 2002.

TECHNICAL FIELD

The disclosed invention relates to the use of electromagnetic radiation to monitor sample systems, and more particularly to improvements in ellipsometer and the like systems which are capable of operating in the Vacuum-Ultra-Violet (VUV) wavelength range as well as in the Visible and near Infrared (NIR) ranges, including methodology of use. Said improvements enable greater ease of application and achieving improved accuracy and precision in obtained results.

BACKGROUND

To begin, it Is disclosed that the inventions or concepts Claimed in or Conceived in Co-Owned Patents:

U.S. Pat. No. 5,757,494 to Green et al.;

U.S. Pat. No. 5,956,145 to Green et al.;

which teach system and method for improving data acquisition capability in spectroscopic ellipsometers;

U.S. Pat. No. 5,872,630 to Johs et al.;

which describes a rotating compensator ellipsometer system and documents conception of the idea of using a quad detector in automated beam alignment;

U.S. Pat. No. 6,034,777 to Johs et al.;

which describes a method of correcting for the effect of windows in a vacuum chamber, hence the application of ellipsometer systems in controlled environment chambers;

U.S. Pat. No. 5,661,589 to Meyer;

which describes a bilateral slit control system which is applied in monochromators; and and in Co-Owned and Co-Pending Allowed patent application Ser. No. 09/531,877;

are revisited in the present Application. Applicant is therefore agreeable to Issue of a Patent on a Terminal Disclaimer basis, where appropriate, in this effort. For instance, it is specifically stated that the invention disclosed in this Application can in many respects, be viewed as the invention in the Co-Pending 877 Application, to which 877 Patent invention is added additional System Elements or Components as limitations.

Continuing, it is of interest to note that Spectroscopic Ellipsometry (SE) was developed in the early 1970's after single wavelength ellipsometry had gained widespread acceptance. The first (SE) systems provided limited Ultraviolet (UV) to near Infrared (IR) spectral range capability, and with the exception of a few research instruments, this remained the case until the 1990's. Many challenges faced development of (VUV) ellipsometer systems, including the fact that many optical element materials absorb in the (VUV) wavelength range. Vacuum Ultraviolet (VUV) ellipsometry was so named as it was initially carried out in vacuum, however, the terminology is today applied where purging gas such as nitrogen is utilized in place of vacuum at wavelengths, typically with an energy less than about 10 ev. The reason (VUV) ellipsometry must be carried out in vacuum or purging gas is that (VUV) wavelengths, are absorbed by oxygen and water vapor.

In the mid-1980's a Spectroscopic ellipsometer was constructed at the BESSY Synchrotron in Berlin for application in the (VUV) wavelength range, (eg. 5-35 eV), and in the 1990's Spectroscopic ellipsometry was achieved in the Extreme Ultraviolet (EUV) range, (eg. greater than 35 eV), at KEK-PF. Application of ellipsometry in the (VUV) and (EUV) wavelength ranges remained restricted to said research facilities until in 1999 commercial (VUV) ellipsometer systems became available from companies such as the J. A. Woollam Co. Inc. At present there are approximately twenty-five (VUV) Systems in use worldwide. It is noted that commercial (VUV) instruments, which provided wavelengths down to 146 nm, were introduced in response to the need for bulk material properties at 156 nm, which is utilized in lithography as applied to semiconductor gate oxide production.

A known Patent which provides for use of VUV wavelength electromagnetic radiation through 10 eV is U.S. Pat. No. 6,414,302 B1 to Freeouf.

The practice of ellipsometry, polarimetry, spectrophotometry, reflectometry, scatterometry and the like, using Infrared (IR), (eg. 2-33 micron), and Ultraviolet (UV), (eg. 135-1700 nm), Electromagnetic Radiation Wavelengths, then is, as disclosed above, known. As mentioned, electromagnetic Radiation with wavelengths below about 190 nm is absorbed by atmospheric components such as Oxygen and Water Vapor. Thus, practice of Ellipsometry etc. using UV Wavelengths is typically carried out in vacuum or an atmosphere which does not contain oxygen and/or water vapor or other absorbing components. The J. A. Woollam CO. VUV-VASE, (Registered Trademark), for instance, utilizes a substantially enclosed Chamber which encompasses a substantially enclosed space which during use is purged by Nitrogen and/or Argon or functionally equivalent gas. (Note Nitrogen does not significantly absorb UV Range wavelengths, and Argon is in some respects even a better choice). Further, the source of the electromagnetic radiation in the J. A. Woollam CO. VUV-VASE is preferably a Deuterium Lamp and/or a Xenon Lamp, which produce wavelengths of 115-400 nm, (of which 135-190 nm is used), and up to about 2000 nm, respectively. Specific wavelengths are selected by a J. A. Woollam Co. Monochromator which is a Cherny-Turner type Spectrometer sequentially comprising, mounted inside an enclosing means;

a) source means for providing of a beam including ultraviolet wavelength range electromagnetic radiation;
 b) a first slit;
 c) a first spherical mirror;
 d) a first stage comprising a plurality of gratings, each of which can be rotated into a functional position;
 e) a second spherical mirror;
 f) a second slit;
 g) a third spherical mirror
 h) a second stage comprising a plurality of gratings, each of which can be rotated into a functional position;
 i) a forth spherical mirror; and
 j) a pin hole;

and further comprising a beam chopping means present between said source means and said pin hole;

such that in use an electromagnetic beam from said source of the electromagnetic radiation is:
- caused pass through said first slit;
- reflect from said first spherical mirror;
- interact with one of said plurality of gratings on said first stage which is rotated into a functional position;
- reflect from said second spherical mirror;
- pass through said second slit;
- reflect from said third spherical mirror;
- interact with one of said plurality of gratings on said second stage which is rotated into a functional position;
- reflect from said forth spherical mirror; and
- exit through said pinhole;

and at some point in said progression be subjected to chopping.

The gratings on said first and second stages are separately rotated into precise desired functional positions via stepper motors controlled by computer. This has proven to provide superior precision, repeatability and speed of achieving the desired wavelength than commercially available grating positioning systems in which both gratings are simultaneously controlled. Further, an electromagnetic radiation beam produced by said Monochromator has been shown to provide a highly collimated beam, with typical defining parameters being a 5 mm diameter at the pinhole output of the Monochromator, with divergence to about 20 mm diameter at 20 Feet, (ie. 6000 mm). This represents a divergence angle of only about 0.00125 radians, (ie. 0.07 Degrees).

It is further disclosed that the chopper means comprises a lock-in amplifier which chops the electromagnetic beam at a frequency which is synchronized to a detector which receives the electromagnetic beam after it interacts with a sample, (see further below). The synchronization is typically without delay, but there can be a phase relationship introduced between the beam chopping and the detection of the signal by the detector. Said lock-in amplifier is utilized to provide a better signal to noise ratio. The use of a chopping lock-in amplifier is beneficial in that background noise is eliminated. For instance, if said approach is not used it can be necessary to obtain data in a darkened room and to avoid the influence of extraneous electromagnetic radiation, or if data is obtained in a lighted room an additional background data set must be obtained using a shutter to block the beam, and then a subtraction procedure applied to compensate the data set for the background extraneous electromagnetic influence. Where chopping is utilized data can be obtained in a lighted room without the need to obtain an additional data set and apply the subtraction procedure.

Application problems have been identified with the design of the monochromator system as described, in that wiring and electronic components have to date been included inside the substantially enclosed space within the enclosure. Outgassing from wiring and electronic components etc., (as required where Vacuum-Ultraviolet (VUV) wavelengths are utilized), can require very long periods of time. Further, electrical connections to components such as the means for providing the first and second slits and rotating effecting means for the first and second stage which comprises thereupon a plurality of gratings, to date, have been hard wired thereto, thereby making replacement tedious. As insight, at this point it is noted that improvements disclosed herewithin include the use of a wire eliminating "Mother Board" inside the substantially enclosed space within the monochromator system, to which Mother Board components electrical connections are via easily removable plug-socket means. Further, electronic components are mounted to a Second Printed-Circuit Board which is mounted outside said enclosure via plug-in means, thereby making its replacement easy to accomplish without requiring opening the substantially enclosed space within the enclosure to atmosphere.

A problem with practicing Ellipsometry etc. where the sample system is in a substantially enclosed, internal ambient controlled, chamber is that it is very inconvenient to access what is contained therewithin without entering oxygen or water vapor etc. thereinto. As a result, the J. A. Woollam Co. VUV-VASE, (Registered Trademark), System comprises a means for causing a subspace sequestering means to become configured so as to sequester a sample system in a subspace of said substantially enclosed space during entry and removal of a sample system. This allows accessing a sample system means for placing and maintaining a sample system in a desired position and orientation, (ie. a sample supporting stage), with the benefit that only the sequestered subspace then needs substantial purging. The subspace sequestering means further enables reconfiguration to open the entire substantially enclosed space in the chamber to the sample system, thereby facilitating its access thereof via UV range wavelength electromagnetic radiation.

It is noted that the J. A. Woollam Co. VUV-VASE has proven to provide good data in cases even when operated without Nitrogen purging, and has been applied to obtain reflection data using an electromagnetic beam caused to approach a sample system at a normal or oblique angle of incidence, transmission data with an electromagnetic beam being caused to approach a sample system at a normal or oblique angle of incidence, using unpolarized electromagnetic radiation, or partially polarized electromagnetic radiation or polarized electromagnetic radiation. That is, very good data has been obtained utilizing unpolarized; partially polarized, randomly polarized; linearly polarized; with respect to a sample system linearly "p" polarized; with respect to a sample system linearly "s" polarized; and circularly polarized electromagnetic radiation in purged and atmospheric ambients.

The J. A. Woollam Co. VUV-VASE includes two-speed purge control means, such that a sequestered subspace can be purged, quickly, but when purging is substantially complete, a Nitrogen conserving slower maintenance purge speed can be effected.

It is further disclosed that versions of the J. A. Woollam CO. VUV-VASE which have been sold to date have included a Quad Detector having a centrally located hole therein which is 1.27 mm in diameter, which Quad Detector is mounted via a stepper motor means for moving the centrally located hole into and out of the locus of a beam of electromagnetic radiation. The Quad Detector has Four Detector Elements surrounding the centrally located hole. In use a sample system is oriented by a means for placing and maintaining a sample system in a desired position and orientation, (typically comprising a vacuum chuck to secure the sample), such that a beam of electromagnetic radiation which passes through the centrally located hole in the Quad Detector reflects directly 180 degrees back, thereby minimizing the amount of energy entering the Detector Elements. Once the sample system is so oriented, the sample system is caused to be rotated so that a perpendicular to its surface is redirected by a known number of degrees. This procedure allows setting a precise Angle-Of-Incidence of the electromagnetic beam to the sample system surface without the requirement of calibration. However, the small diameter of the centrally located hole in the Quad Detector can not be left in place during data acquisition as it reduces the intensity of the beam an unacceptable amount. Thus, versions of the J. A. Woollam CO. VUV-VASE available to date have included the mentioned motorized means inside the substantially closed Chamber to move the Quad Detector completely away from the locus of the electromagnetic beam after alignment is complete. This has led to problems such as Quad Detector socket pins eventually not lining-up properly with socket holes etc. While mounting and removing a Quad Detector is easy to practice in open air it is not convenient in a substantially enclosed space which requires purging every time it is opened to, for instance, straighten electrical pins on a Quad Detector. It is noted at this point that the disclosed invention newly provides a previously undisclosed specially designed permanently mounted Quad Detector with a larger, (eg. 2-4 mm diameter), centrally located, hole therewithin through which a beam of electromagnetic radiation can be passed during data acquisition. It has been found that about ten (10) times more electromagnetic radiation intensity passes through said larger 2-4 mm diameter hole than does through said 1.27 mm diameter hole. Further, excellent angle of incidence alignment by the procedure described above is still achievable using the new quad detector.

It is noted at this point that a Patent to Johs et al. U.S. Pat. No., 5,872,630, from which this Application Continues-In-Part via other Co-Pending Applications, in Col. 20, Lines 55-57, establishes conception of the idea of applying a Quad Detector in an Automated Beam Alignment Procedure in the context of an Ellipsometer System. A fixed Quad Detector applied in an Automated Alignment Procedure which incorporates use of stepper motors to, in response to Quad Detector System Detector Elements, automatically align a Sample System, has not been previously available. This is particularly true in two cases:

where a fixed location Quad Detector with a relatively large, (eg. 2-4 mm diameter as compared to a standard 1.27 mm hole diameter), centrally located hole therein, through which an electromagnetic beam passes during both Alignment and Data Acquisition, and where a Quad Detector is placed so that the electromagnetic beam does not pass therethrough during Alignment or Data Acquisition, but rather is placed such that a beam which approaches a Sample System at an oblique angle enters thereinto.

It is noted that while the later scenario is of benefit in that absolutely no attenuation of an electromagnetic beam is caused during Data Acquisition by the Quad Detector, it becomes necessary to then Calibrate the relationship between said oblique angle, and the orientation of the Sample System, to then enable orienting the Sample system so an electromagnetic beam approaches along a known angle of incidence thereto during Data Acquisition. Where an electromagnetic beam passes through a centrally located hole in a Quad Detector, once the Sample System is aligned so that it reflects a beam directly back 180 degrees from a surface of a Sample System, it is a relatively simple matter to then re-orient the Sample System with respect to said aligned Sample System orientation to effect a desired Angle-Of-Incidence of the electromagnetic beam to said Sample System. Hence, while placing a Quad Detector so that an electromagnetic beam does not have to pass through a centrally located hole therein enables avoiding attenuating beam intensity, said placement initiates the need to then perform a calibration procedure. It is also noted that a Quad Detector through which an electromagnetic beam need not pass, need not have a centrally located hole therein or can have a standard 1.27 mm in diameter hole therethrough, and hence can enable tighter positioning of Detector elements therein, thereby enabling slightly greater precision in Alignment than can be the case where a greatly larger diameter hole is present.

The J. A. Woollam CO. VUV-VASE is further fitted with a multiple detector system as described in Co-Owned and Co-Pending Allowed patent application Ser. No. 09/531,877, which comprises a plurality of Detectors. The purpose is to allow easily rotating one of a plurality of Detectors into position to receive a beam of electromagnetic radiation after interaction with a sample system. Preferably each Detector has associated therewith an Analyzer, but it is possible to provide a single separately mounted Analyzer with only the plurality of Detectors. The ability to move Detectors in and out of a beam, enables easy sequential positioning of Detectors which are sensitive in different wavelength ranges. It is also noted that the ability to easily move a Detector facilitates use in "Scaterometry", wherein an electromagnetic beam is caused to interact with a sample system in a substantially fixed manner, while the Detector system is moved through a plurality of positions, at each of which positions data is obtained thereby. Electromagnetic radiation scattered to each said location is thus separately monitorable by a movable detector.

The J. A. Woollam CO. VUV-VASE System has utilized Detector Elements of Stacked construction for years, (eg. Si/GaAs, Si/InP, and Si/InGaAs. Proposed is use of Si/Strained InGaAs to enable detecting 2.2 micron in the J. A. Woollam IR-VASE (Registered Trademark) Ellipsometer System which operates in the electromagnetic wavelength range of 2-33 microns. Also proposed is use of Three (3) layer Stacked Detector Elements.

The J. A. Woollam IR-VASE System provides Dual Detector capability, variable Angle-Of-Incidence capability and utilizes an Alignment mechanism in which a Laser beam is entered thereinto by way of an externally mounted Laser Source and Mirror combination. Once Alignment is accomplished using the highly collimated Laser beam, the Mirror is reoriented to allow entry of polychromatic IR wavelength range electromagnetic radiation. In that light it is disclosed that it is known to provide a source of electromagnetic radiation and cause it to reflect perpendicularly from a surface of a sample so that the orientation of the source of the electromagnetic beam is known, then to rotate/tilt the sample to set it such that said electromagnetic beam approaches it along an oblique angle, and then to move the sample in a direction perpendicular to its surface so that a reflected electromagnetic beam enters a present data detector. Said technique is utilized in the J. A. Woollam CO. VUV-VASE System, for instance. It is also known to focus a beam of electromagnetic radiation which approaches a surface of a sample onto a very small spot and reflects therefrom, and without tending to any sample rotation/tilting move the sample along a substantial perpendicular to said sample surface until a reflected beam optimally enters a present detector. Where a focused beam is utilized the spot size is sufficiently small that a slight tilt of the sample has little effect on the trajectory of the reflected beam. This technique is utilized in systems produced by Nanometrics Inc.

As alluded to, where UV wavelength range electromagnetic radiation is utilized., the atmosphere can not be allowed to contain Oxygen or $H_2O$ vapor. As materials such as electrical wire coatings generally absorb such components, the J. A. Woollam CO. VUV-VASE is presently being re-designed to place 30 substantially all electrical wiring, and other such materials, outside the substantially enclosed chamber. This enables relatively quick purging with such as Nitrogen or Argon and reduces contamination that otherwise might accumulate on sensitive optical surfaces and/or samples under study.

Another feature of the J. A. Woollam CO. VUV-VASE is that the electromagnetic beam is chopped by a lock-in-frequency and phase sensitive amplifier which is synchronized with detection. This enables a modulation signal, typically at 266 Hz, which is demodulated by detector related circuitry. It is noted that the J. A. Woollam CO. VUV-VASE utilizes a Rotating Analyzer which is rotated during data acquisition at 14.88 Hz, a much lower rate than is the chopping frequency and that the modulation produces sidebands at (266+/−14.88) HZ of which one is usually utilized. It is also noted that typically data is acquired over a 300 Analyzer rotation period, and an averaged value is provide.

The J. A. Woollam CO. VUV-VASE utilizes a Touch Screen Control approach, although key or mouse aided or any functional means for entry of control instructions can be utilized.

Both the J. A. Woollam CO. VUV-VASE and IR-VASE Systems typically include an Auto-Retarder System which enables said Rotating Analyzer based Systems to obtain data in ranges in which conventional Rotating Polarizer and Rotating Analyzer Ellipsometer Systems alike have been unable to provide reliable accurate and/or precise data. The Auto-Retarder is sequentially positioned after a Stepwise Rotatable Polarizer and enables sequentially modifying a polarization state set by said polarization state setting means, through a plurality of polarization states. Said Auto-Retarder is described in Patent to Green U.S. Pat. No. 5,956,145, and comprises a selected from the group consisting of:

a. at least one Variable Retarder(s) positioned such that said at least one Variable Retarder(s) and Sample System per se. form a Composite Sample System as seen by said ellipsometer system, and such that a Sample System analyzing polarized light beam is caused to interact with said at least one Variable Retarder(s) and Sample System per se. during use, thereby experiencing a polarization state change; which said at least one Variable Retarder(s) is selected from the group consisting of:
      a. a system of at least two waveplate-type Retarders selected from the group consisting of zero-order-waveplate-type Retarders and multi-order-waveplate-type Retarders, which waveplate-type retarders can be rotated with respect to one another, each about an axis perpendicular to an Optical axes thereof, said Optical axes being essentially parallel to the surface of said waveplate-type Retarders;
      b. a Babinet dual wedge-type Variable Retarder;
      c. a Soleil dual wedge-type Variable Retarder;
      d. a Kerr electro-optical-type Variable Retarder;
      e. a Pockels electro-optical-type Variable Retarder;
      f. a Liquid Crystal electro-optical-type Variable Retarder;
      g. a Voigt magnetic-Faraday-effect Variable Retarder;
      h. a Cotton-Mouton magnetic-Faraday-effect Variable Retarder;
      i. a Berek-type Variable Retarder, the optical axis of which is oriented essentially perpendicular to the surface thereof, which Berek-type Retarder can be tilted about multiple axes to align said optical axis such that it is coincident with an incident polarized beam of light and thereby cause only a negligible attenuation effect, rather than a polarization state changing effect thereon; and such that in use adjusting of a present said at least one Variable Retarder(s) places at least the DELTA of said Composite Sample System is placed within a range in which the PSI and DELTA of said Composite Sample System can be usably accurately and precisely investigated by said ellipsometer system.

Finally, additional Patents disclosed for general background background are: U.S. Pat. No. 5,582,646 to Woollam et al.; U.S. Pat. No. 5,963,327 to He et al.; U.S. Pat. No. 6,456,376 to Liphardt et al.; U.S. Pat. No. 5,582,646 to Woollam et al.; U.S. Pat. No. 4,210,410 to Batten; U.S. Pat. No. 5,045,704 to Coates; U.S. Pat. No. 5,045,701 to Goldstein et al.; U.S. Pat. No. 4,472,633 to Motooka; U.S. Pat. No. 5,486,701 to Norton et al.; U.S. Pat. No. 5,706,212 to Thompson et al.; and Application US2002/0024668 A1 of Stehle et al.

Even in view of the prior art, need remains for improvements on, additions to and new combinations of described ellipsometer and the like systems and methods. Said improvements being, for instance, in the areas of systems and methods involving monochromators, sample alignment, the setting of angles of incidence of a beam to a sample, use of environment control chambers and signal detectors.

DISCLOSURE OF THE INVENTION

In general, it should be appreciated that ellipsometer and polarimeter systems can be configured for use in both reflection and transmission modes and comprise a source of monochromatic or polychromatic electromagnetic radiation and via polarization state modifier, typically a Polarizer and optional Compensator, provides a polarized beam of electromagnetic radiation which is directed to interact with a material system which is placed on a stage. The combined Source and Polarization State Modifier is typically termed a Polarization State Generator. After interaction with a material system, a propagated electromagnetic beam passes through a polarization state analyzer and optional compensator, and enters a Detector System. The combined polarization state analyzer and Detector System is typically termed a Polarization State Detector system. Where polarization state setting polarizer and optional compensator and analyzer and optional compensator are-absent the resulting system can be termed a spectrophotometer system.

VACUUM ULTRAVIOLET (VUV) ELLIPSOMETER SYSTEM

As a specific example of a disclosed invention ellipsometer system for analyzing sample systems using electromagnetic radiation with wavelengths in the ultraviolet wavelength range, said ellipsometer system can be described as comprising a chamber means which encompasses a substantially enclosed space, functionally within said substantially enclosed space there being present:

a) source means for providing of a beam including ultraviolet wavelength range electromagnetic radiation;

b) polarization state setting means for setting a polarization state in at least a selected small range of wavelengths in a beam including ultraviolet wavelength range electromagnetic radiation;

c) means which enables sequentially modifying a polarization state set by said polarization state setting means, through a plurality of polarization states;

d) alignment detector means comprising a plurality of detector elements surrounding a substantially centrally located hole through which a beam of electromagnetic radiation can pass, said substantially centrally located hole having a diameter sufficiently large such that about ten times more intensity of a beam passes therethrough than does through a hole of 1.27 mm;

e) a means for placing and maintaining a sample system in a desired position and orientation, (optionally a vacuum chuck), said means for placing and maintaining a sample system in a desired position and orientation being positioned in a subspace of said substantially enclosed space which can be sequestered by a subspace sequestering means;

f) data detector means for receiving an electromagnetic beam which is caused to interact with a sample system which is secured in place by said means for placing and maintaining a sample system in a desired position and orientation; and g) computer means for analyzing data provided by said data detector means for receiving an electromagnetic beam after it interacts with said sample system;

h) monochromator means, for selecting a small range of wavelengths in a beam including ultraviolet wavelength range electromagnetic radiation, present between said source means for providing of a beam including ultraviolet wavelength range electromagnetic radiation and said data detector means for receiving an electromagnetic beam which is caused to interact with a sample system.

Said chamber means has functionally affixed thereto means for causing said subspace sequestering means to become configured so as to sequester a sample system in a subspace of said substantially enclosed space, or to open and expose said sample system generally to the substantially enclosed space, and means for accessing said means for placing and maintaining a sample system in a desired position and orientation.

Said chamber further has means having functionally affixed thereto means for entering purging gas into said substantially enclosed space generally, and to a subspace sequestered by said subspace sequestering means independently when it is caused to be sequestered from said substantially enclosed space.

In use a sample system is caused to be affixed to said means for placing and maintaining a sample system in a desired position and orientation via said means for accessing said means for placing and maintaining a sample system in a desired position and orientation, and purging gas is caused to be entered into said substantially enclosed space via said means for entering purging gas into said substantially enclosed space generally, and/or to a subspace sequestered by said subspace sequestering means independently when it is caused to be sequestered from said substantially enclosed space, and said source means for providing of a beam including ultraviolet wavelength range electromagnetic radiation is caused to provide a beam including ultraviolet wavelength, and said polarization state setting means for setting a polarization state in a selected small range of wavelengths in a beam including ultraviolet wavelength range electromagnetic radiation is caused to impose a polarization state thereupon and said beam of ultraviolet wavelength range electromagnetic radiation is caused to pass through said hole in said alignment detector means comprising a plurality of detector elements surrounding a substantially centrally located hole, and said monochromator means for selecting a small range of wavelengths in said beam of ultraviolet wavelength range electromagnetic radiation is caused to provide a small range of wavelengths in said beam of ultraviolet wavelength range;

such that said means for placing and maintaining a sample system in a desired position and orientation is caused to orient said sample system so that said beam including ultraviolet wavelength range electromagnetic radiation is caused to reflect essentially directly back from said sample system such that the signals from each of the alignment detector means of said plurality of detector elements provide optimum signal output, and then, without removing said alignment detector means of said plurality of detector elements, causing said means for placing and maintaining a sample system in a desired position and orientation is caused to reorient said sample system such that said beam including ultraviolet wavelength range electromagnetic radiation impinges thereupon at a known angle of incidence;

and such that said beam including ultraviolet wavelength range electromagnetic radiation interacts with said sample system and then enters said data detector.

An improvement over prior art is the inclusion of the permanently mounted alignment detector means which comprises a plurality of detector elements surrounding a substantially centrally located hole through which a beam of electromagnetic radiation can pass. It has been found that where the centrally located hole is of a diameter greater than 1.27 mm, (eg. between 2-4 mm diameter), alignment can be accomplished without an accompanying attenuation of the electromagnetic beam which passes therethrough during data collection.

Preferred source means for providing of a beam of ultraviolet wavelength range electromagnetic radiation is selected from the group consisting of:

a Xenon lamp; and a Deuterium lamp.

The monochromator means for selecting a small range of wavelengths in a beam including ultraviolet wavelength range electromagnetic radiation is typically present between said source means for providing of a beam including ultraviolet wavelength range electromagnetic radiation and said alignment detector means, and sequentially comprises inside an enclosing means:

a) a first slit;

b) a first spherical mirror;

c) a first stage comprising a plurality of gratings, each of which can be rotated into a functional position;

d) a second spherical mirror;

e) a second slit;

f) a third spherical mirror g) a second stage comprising a plurality of gratings, each of which can be rotated into a functional position;

h) a forth spherical mirror; and i) a pin hole;

and further comprising a beam chopping means present between said source means and said pin hole;

such that in use an electromagnetic beam is:

caused to pass through said first slit;

reflect from said first spherical mirror;

interact with one of said plurality of gratings on said first stage which is rotated into a functional position;

reflect from said second spherical mirror;
pass through said second slit;
reflect from said third spherical mirror;
interact with one of said plurality of gratings on said second stage which is rotated into a functional position;
reflect from said forth spherical mirror; and
exit said pin hole;

and at some point between said source means and pin hole said electromagnetic beam being chopped;

the improvements being that a "Mother Board" inside said enclosing means provides easily removable plug-in means for providing electrical signals and power to stepper motors in said first and second slit effecting means and rotation effecting means for each of said first and second stages which comprise a plurality of gratings.

The means which enables sequentially modifying a polarization state set by said polarization state setting means, through a plurality of polarization states, is typically selected from the group consisting of:
 a. at least one Variable Retarder(s) positioned such that said at least one Variable Retarder(s) and Sample System per se. form a Composite Sample System as seen by said ellipsometer system, and such that a Sample System analyzing polarized light beam is caused to interact with said at least one Variable Retarder(s) and Sample System per se. during use, thereby experiencing a polarization state change; which said at least one Variable Retarder(s) is selected from the group consisting of:
  a. a system of at least two waveplate-type Retarders selected from the group consisting of zero-order-waveplate-type Retarders and multi-order-waveplate-type Retarders, which waveplate-type retarders can be rotated with respect to one another, each about an axis perpendicular to an Optical axes thereof, said Optical axes being essentially parallel to the surface of said waveplate-type Retarders;
  b. a Babinet dual wedge-type Variable Retarder;
  c. a Soleil dual wedge-type Variable Retarder;
  d. a Kerr electro-optical-type Variable Retarder;
  e. a Pockels electro-optical-type Variable Retarder;
  f. a Liquid Crystal electro-optical-type Variable Retarder;
  g. a Voigt magnetic-Faraday-effect Variable Retarder;
  h. a Cotton-Mouton magnetic-Faraday-effect Variable Retarder;
  i. a Berek-type Variable Retarder, the optical axis of which is oriented essentially perpendicular to the surface thereof, which Berek-type Retarder can be tilted about multiple axes to align said optical axis such that it is coincident with an incident polarized beam of light and thereby cause only a negligible attenuation effect, rather than a polarization state changing effect thereon; and such that in use adjusting of a present said at least one Variable Retarder(s) places at least the DELTA of said Composite Sample System is placed within a range in which the PSI and DELTA of said Composite Sample System can be usably accurately and precisely investigated by said ellipsometer system.

The alignment detector means typically comprises a plurality of detector elements surrounding a substantially centrally located hole through which a beam of electromagnetic radiation can pass is a quad-detector and the centrally located hole has a diameter of, for instance, between two (2) and four (4) mm which allows about ten times more intensity of a beam to pass therethrough than does through a hole of 1.27 mm.

The first and second slits are typically effected by a bilateral slit assembly which comprises two slide assemblies, each slide assembly comprising an elongated rail element and a slide element such that said slide element can slide with respect to said elongated rail element in the direction of elongation thereof, wherein said two slide assemblies are oriented, by affixing said elongated rail elements to a frame, such that slide element's loci of motion converge toward a lower extent of said frame, as said bilateral slit assembly is viewed in vertically oriented frontal elevation, thereby forming an upward opening "V" shape therebetween, the lower ends of each slide element comprising means for allowing horizontal motion therebetween when said slide element lower ends are caused to simultaneously move vertically during use, which bilateral slit assembly further comprises two knife-blade elements, one affixed to each slide element such that a horizontal slit width between vertically oriented facing edges of said two knife-blade elements can be controlled between essentially zero (0) distance and some larger distance by a simultaneous vertically oriented motion of the lower ends of said slide elements during use;

the purpose of controlling said horizontal slit width between vertically oriented facing edges of said two knife-blade elements being to control the intensity and frequency bandwidth of a light beam which can pass therebetween, as is required by spectrometers, monochromators, and spectrographs and the like.

The means for causing the simultaneous motion of said slide elements during use is a precisely controlled computer driven stepper motor which causes a threaded motor shaft therein to move vertically as a result of screw thread translation of motor imparted rotational motion to said threaded motor shaft, said vertical motion causing said slide elements to simultaneously move vertically during use, said precisely controlled computer driven stepper motor being firmly affixed to said frame so that the relative positioning between it and the slide assemblies is rigidly fixed during use.

The disclosed invention can also comprise a means for generating an electromagnetic beam in a:
 reflectometer;
 spectrophotometer;
 ellipsometer;
 spectroscopic ellipsometer;
 polarimeter;.and
 spectroscopic polarimeter;

and means for causing it to impinge upon a sample system, said system comprising, prior to said sample system, at least one spatial filter which serves to attenuate an outer annular region from said electromagnetic beam as it passes therethrough;

said system being further characterized by a selection from the group consisting of:
 said at least one spatial filter is positioned prior to a beam directing reflective means which directs said electromagnetic beam onto said sample system; and
 there is no beam directing reflective means present prior to
 said sample system which directs said electromagnetic beam onto said sample system;

wherein said spatial filter sequentially comprises:
  first beam collimating lens;
  aperture;
  beam converging at least one lens and/or mirror;
  diaphragm with a pin hole therein located essentially at the focal length of said at least one beam converging lens and/or mirror; and
  second beam collimating at least one lens and/or mirror;
  ps such that in use the central portion of the electromagnetic beam which is collimated by said first beam collimating lens is caused to pass through said aperture, become focused on and at least partially pass through said pin hole in said diaphragm by said beam converging at least one lens and/or mirror, and become recollimated by said second beam collimating at least one lens and/or mirror.

The spatial filter system can be applied to a selection from the group consisting of:
  reflectometer;
  spectrophotometer;
  ellipsometer;
  spectroscopic ellipsometer;
  polarimeter; and
  spectroscopic polarimeter;
which generates an electromagnetic beam and causes it to impinge upon a sample system, said system comprising, prior to said sample system, at least one spatial filter which serves to attenuate an outer annular region from said electromagnetic beam as it passes therethrough;

said system being characterized by a selection from the group consisting of:
  said at least one spatial filter(s) is positioned prior to a said sample system; and
  said at least one spatial filter(s) is positioned prior to a said sample system.

Alternatively, the system which generates an electromagnetic beam and causes it to impinge upon a sample system, said system comprising, prior to said sample system, at least one spatial filter which serves to attenuate an outer annular region from said electromagnetic beam as it passes therethrough, can be distinguished as comprising a collimating means and an aperture means prior to said sample, and a converging means after said sample which focuses the electromagnetic beam onto the end of an optical fiber which transmits entering electromagnetic radiation to at least one detector.

It is specifically noted that while not limiting, the Stage for securing a Sample System can conveniently include a vacuum chuck which allows easily securing and releasing the sample by providing a suction, or not. In addition, the Stage for securing a Sample System can also contain a heating and/or cooling means for controlling the temperature of a sample.

METHODOLOGY OF APPLYING VACUUM ULTRAVIOLET ELLIPSOMETER SYSTEM

A method of analyzing a sample system using a beam of electromagnetic radiation with wavelengths in the ultraviolet wavelength range can comprise the steps of:
  A) providing an ellipsometer system for analyzing sample systems using electromagnetic radiation with wavelengths in the ultraviolet wavelength range as described above;
  B) via said means for causing said subspace sequestering means to become configured so as to sequester a sample system in a subspace of said substantially enclosed space, or to open and expose said sample system generally to the substantially enclosed space, entering a sample system to said subspace;
  C) via said means for entering purging gas into said substantially enclosed space generally, and to a subspace sequestered by said subspace sequestering means independently when it is caused to be sequestered from said substantially enclosed space, purging said substantially enclosed space generally, and said subspace sequestered by said subspace sequestering means in particular until the subspace sequestered by said subspace sequestering means is sufficiently purged to be substantially free of oxygen and water vapor, followed by, if necessary, opening said subspace sequestered by said subspace sequestering means to the substantially enclosed space generally;

practicing steps D) and (E) in either order:
  D) using said source means for providing of a beam of ultraviolet wavelength range electromagnetic radiation, and monochromator means for selecting a small range of wavelengths in a beam including ultraviolet wavelength range electromagnetic radiation, and said polarization state setting means for setting a polarization state in a selected small range of wavelengths in a beam including ultraviolet wavelength range electromagnetic radiation, and said means which enables sequentially modifying a polarization state set by said polarization state setting means, through a plurality of polarization states providing a beam of electromagnetic radiation of a known wavelength in the ultraviolet range to exit said hole in said alignment detector means which comprises a plurality of detector elements surrounding said substantially centrally located hole; and
  E) via said means for placing and maintaining a sample system in a desired position and orientation, causing said sample system to be oriented so that a surface thereof is oriented roughly perpendicular the locus of said beam of electromagnetic radiation of a known wavelength in the ultraviolet range and adjusting said orientation of said sample system such that signals developed by the plurality of detector elements in said alignment detector means indicate that said surface of said sample system is oriented substantially perpendicular to said locus of said beam of electromagnetic radiation of a known wavelength in the ultraviolet range;
  F) causing said means for placing and maintaining a sample system in a desired position and orientation, to rotate said sample system, (manually or under computer control via goniometer and stepper motors), so that said beam of electromagnetic radiation of a known wavelength in the ultraviolet range approaches said surface of said sample system at a known angle-of-incidence thereto which is referenced to the orientation of said sample system when the beam of electromagnetic radiation of a known wavelength in the ultraviolet range was caused to approach said surface of said sample system along a locus substantially perpendicular thereto;
  G) intercepting said beam of electromagnetic radiation of a known wavelength in the ultraviolet range with said data detector means for receiving an electromagnetic beam which is caused to interact with a sample system secured in place by said means for placing and maintaining a sample system in a desired position and orientation;

H) using said computer means for analyzing data provided by said data detector means for receiving an electromagnetic beam after it interacts with said means for maintaining a sample system in a desired position and orientation, analyzing said date provided by said data detector means.

Said method of analyzing a sample system using a beam of electromagnetic radiation with wavelengths in the ultraviolet wavelength can be applied to a sample system characterized by a selection from the group consisting of:
  isotropic and non-depolarizing, (characterized by a Jones Matrix);
  isotropic and depolarizing;
  anisotropic and non-depolarizing;
  anisotropic and depolarizing, (thereby requiring a full Mueller Matrix characterization);

in which the beam of electromagnetic radiation provided by said source means for providing of a beam including ultraviolet wavelength range electromagnetic radiation, is characterized by a selection from the group consisting of:
  it comprises a single wavelength;
  it comprises multiple wavelengths;
  it comprises a plurality of scanned wavelengths which are sequentially scanned individually;

and in which the beam of electromagnetic radiation is, just prior to said sample system characterized by a selection from the group consisting of:
  unpolarized;
  partially polarized;
  randomly polarized;
  linearly polarized;
  with respect to said sample system linearly "p" polarized;
  with respect to said sample system linearly "s" polarized;
  circularly polarized;

and is caused to interact with a sample system via a selection from the group consisting of:
  by reflection;
  by transmission;
  by both reflection and transmission;

at one or more angles of incidence, (AOI's), with respect to a surface thereof selected from the group consisting of:
  normal;
  orthogonal;

while said data detector means is utilized to detect resulting:
  reflected;
  transmitted;
  scattered electromagnetic radiation.

The beam of electromagnetic radiation with wavelengths in the ultraviolet wavelength range in which the electromagnetic radiation which is applied to a sample system can further be characterized by being, before and monitored after said sample system, respectively:
  non-polarized incident, with measurement of intensity out;
  non-polarized incident, with measurement of polarized out;
  polarized incident, with measurement of intensity out;
  polarized incident, with measurement of polarized out.

Further, said method of analyzing a sample system using a beam of electromagnetic radiation with wavelengths in the ultraviolet wavelength range can have modulation applied thereto during data accumulation, said modulation being of at least one selection from the group consisting of:
  Electromagnetic Beam Magnetic "B" Field;
  Electromagnetic Beam Electric "E" Field;
  Electromagnetic Beam Flux "$E^2$";
  Ambient Environment Composition, (eg. liquid, gas);
  Sample System Temperature, (which can be above or below room temperature);
  Sample System Strain;
  Pressure applied to Sample System.

Further, said method of analyzing a sample system using a beam of electromagnetic radiation with wavelengths in the ultraviolet wavelength can involve providing polarizer means and accumulating ellipsometric PSI data while ellipsometric DELTA is placed within a range near 90 degrees via adjustment of the angle-of-incidence of the beam of electromagnetic radiation with respect to the surface of said sample system.

A time efficient method of analyzing sample systems with spectroscopic electromagnetic radiation comprised of wavelengths which are absorbed by Oxygen and/or Water Vapor and wavelengths which are not absorbed by Oxygen and/or Water Vapor, comprising the steps of:

in any functional order practicing steps a, a' and a":
  a) providing a chamber which encloses a substantially enclosed space which contains Oxygen and/or Water Vapor, to which chamber is functionally affixed a means for evacuating or purging said substantially enclosed space of oxygen and/or Water Vapor, and means for entering a beam of electromagnetic radiation thereinto, and a means for exiting electromagnetic radiation therefrom; and
  a') providing a source of a spectroscopic beam electromagnetic radiation comprised of wavelengths which are absorbed by Oxygen and/or Water Vapor and wavelengths which are not absorbed by Oxygen and/or Water Vapor; and
  a") providing a data detector of spectroscopic electromagnetic radiation;

and then proceeding to practice steps b and c:
  b) positioning a sample system in said substantially enclosed space;
  c) while causing said means for evacuating or purging said substantially enclosed space of Oxygen and/or Water Vapor to evacuate or purge said substantially enclosed space of Oxygen and/or Water Vapor, causing said source of a spectroscopic beam electromagnetic radiation comprised of wavelengths which are absorbed by Oxygen and/or Water Vapor and wavelengths which are not absorbed by Oxygen and/or Water Vapor, to provide a beam of said electromagnetic radiation comprised of wavelengths which are absorbed by Oxygen and/or Water Vapor and wavelengths which are not absorbed by Oxygen and/or Water Vapor and cause it to enter said means for entering a beam of electromagnetic radiation along a locus, such that it interacts with said sample system and exits said means for exiting electromagnetic radiation and enters said detector of spectroscopic electromagnetic radiation;

such that during the evacuation or purging process, while Oxygen and/or Water Vapor is still present in said substantially enclosed space in sufficient quantity to absorb said wavelengths which are absorbed by said Oxygen and/or Water Vapor, data is provided by said data detector for wavelengths which are not absorbed by Oxygen and/or Water Vapor, and such that once said substantially enclosed space is sufficiently evacuated or purged of Oxygen and/or Water Vapor, data is provided by said data detector for wavelengths which are absorbed by Oxygen and/or Water Vapor.

A method of automatically aligning the surface of a sample system with respect to the locus of an incident beam of electromagnetic radiation comprising the steps of:
    a) providing a system which comprises a source of a beam of electromagnetic radiation and an alignment detector, which alignment detector comprises a plurality of detector elements which are positioned to surround a centrally located hole thereof, which centrally located hole has a diameter sufficiently large such that about ten (10) times more intensity of a beam passes therethrough than does through a 1.27 mm diameter hole; said system further comprising computing means to which at least two of said plurality of alignment detector, detector elements are functionally electrically interconnected; said system further comprising a means for supporting and controlling the orientation of the surface of a sample system; said means for supporting and controlling the orientation of the surface of a sample system comprising stepper-motor means which is functionally electrically interconnected to said computing means;
    b) causing said source of a beam of electromagnetic radiation to provide a beam of electromagnetic radiation which is directed to pass through said centrally located hole in said alignment detector, and placing a sample system on said means for supporting and controlling the orientation of the surface of a sample system such that the orientation of the surface of said sample system is approximately perpendicular to the locus of said beam of electromagnetic radiation which is provided by said source of a beam of electromagnetic radiation and passes through said centrally located hole in said alignment detector;
    c) causing said computing means to receive signals from said at least two detector elements of said alignment detector and in response apply signal to said stepper-motor means to the end that said surface of said sample system is caused to be oriented substantially perpendicular to the locus of a beam of electromagnetic radiation which is provided by said source of a beam of electromagnetic radiation and passes through said centrally located hole in said alignment detector;
    d) as necessary repeating step c) to the end that said surface of said sample system is caused to be oriented to at least within +/−0.1 degree, (typically better), perpendicular to the locus of a beam of electromagnetic radiation which is provided by said source of a beam of electromagnetic radiation and passes through said centrally located hole in said alignment detector;
    e) causing said stepper motor means to re-orient the surface of said sample system so that a normal thereto is directed at a selected number of degrees with respect to the orientation of said locus of said beam of electromagnetic radiation which is provided by said source of a beam of electromagnetic radiation and passes through said centrally located hole in said alignment detector;

such that said beam of electromagnetic radiation approaches said surface of said sample system at a known angle of incidence thereto.

Another method of automatically aligning the surface of a sample system with respect to the locus of an incident beam of electromagnetic radiation comprises the steps of:
    a) providing a system which comprises a source of a beam of electromagnetic radiation and an alignment detector,,which alignment detector comprises a plurality of detector elements distributed about a central location, said system further comprising computing means to which at least two of said plurality of alignment detector, detector elements are functionally electrically interconnected, said system further comprising a means for supporting and controlling the orientation of the surface of a sample system; said means for supporting and controlling the orientation of the surface of a sample system comprising stepper-motor means being functionally electrically interconnected to said computing means;
    b) causing said source of a beam of electromagnetic radiation to provide a beam of electromagnetic radiation which is directed toward said means for supporting and controlling the orientation of the surface of a sample system and placing a sample system on said means for supporting and controlling the orientation of the surface of a sample system such that the orientation of the surface of said sample system is at an oblique angle to the locus of said beam of electromagnetic radiation, such that said beam reflects from said sample system and proceed toward said alignment detector;
    c) causing said computing means to receive signals from said at least two detector elements of said alignment detector and in response apply signal to said stepper-motor means to the end that said surface of said sample system is caused to be oriented such that approximately equal signals are provided by said at least two detector elements of said alignment detector;
    d) as necessary repeating step c to optimize detector element signal equality;
    e) causing said stepper motor means to re-orient the surface of said sample system a selected number of degrees with respect to the orientation of said locus of said beam of electromagnetic radiation which is provided by said source of a beam of electromagnetic radiation;

such that said beam of electromagnetic radiation approaches said surface of said sample system at a known angle of incidence thereto.

Said methodology of automatically aligning the surface of a sample system with respect to the locus of an incident beam of electromagnetic radiation is preferably conducted utilizing an alignment detector with a plurality of detector elements, (when four are present and it is termed a "quad-detector).

Another method of aligning an electromagnetic beam is focused on aligning a stage/sample, (eg. a large area flat panel for instance), with respect to a beam of electromagnetic radiation, but utilizes two beam of electromagnetic radiation. A Multi-element, (eg. Quad-Detector), sensor system again allows for entering a first beam of electromagnetic radiation through a centrally located opening therein and causes said beam to approach and reflect from the surface of the sample. Said method then provides that the stage/sample be then tilted until the first electromagnetic beam reflects directly back therefrom and therefore does not enter any of the Multiple Detectors which surround the centrally located opening. This determines the orientation of the surface of the with respect to said first electromagnetic beam. The system further provides a source of a second beam of electromagnetic radiation, (it being oriented with respect to the first beam of electromagnetic radiation in a known way), from which a second beam of electromagnetic radiation is caused to approach the surface of the sample at an oblique angle, reflect therefrom and proceed generally toward a provided detector. The method then provides for moving the stage/sample along a perpendicular to the surface of the sample until the data detector is found to receive an electromagnetic beam of a maximum intensity.

Said system for aligning a sample can be described as comprising:
- a pivot mounted stage/sample; and
- a means for imparting translation motion to said pivot mounted stage/sample substantially along a perpendicular to a surface thereof;
- a first source of a first beam of electromagnetic radiation in functional combination with a Quad Detector comprised of at least four detector element surrounding a hole therethrough; and
- a second source of a second beam of electromagnetic radiation; and
- a data detector.

The first source of a first beam of electromagnetic radiation is oriented so as to provide a first beam of electromagnetic radiation through a hole in said Quad Detector, wherein said Quad Detector is comprised of at least four detector elements surrounding said hole therethrough. The pivot mounted stage/sample is positioned to receive said first beam of electromagnetic radiation substantially along a normal to a surface of said pivot mounted stage/sample via said hole in said quad detector. Said second source of electromagnetic radiation is positioned to provide a beam of electromagnetic radiation and direct it to the surface of said sample at an oblique angle thereto, such that said second beam of electromagnetic radiation reflects from said surface of said pivot mounted stage/sample. The first and second electromagnetic beams being oriented with respect to one another at a known angle. Said pivot mounted stage/sample is mounted to said means for imparting translation motion such that said pivot mounted stage/sample can be caused to move substantially along a perpendicular to the surface thereof, such that the reflected second beam of electromagnetic radiation enters said data detector.

A method of aligning a sample comprises the steps of:
a) system for aligning a sample as described directly proceeding;
b) causing a first beam of electromagnetic radiation from said first source of a first beam of electromagnetic to pass through said hole in the Quad Detector such that said first beam of electromagnetic radiation reflects from the surface of said pivot mounted stage/sample;
c) pivoting said sample about said stage/sample pivot mounting until signals from ail of the Quad Detector elements are minimized, indicating that said first beam of electromagnetic radiation approaches said surface of said sample along a normal thereto;
d) causing said second source of electromagnetic radiation to provide a beam of electromagnetic radiation and direct it to the surface of said sample at an oblique angle thereto, such that said second beam of electromagnetic radiation reflects from said surface of said pivot mounted stage/sample;
e) causing said pivot mounted stage/sample to undergo translation motion substantially perpendicular to the surface of said sample via said means for imparting translation motion to said pivot mounted stage/sample;

such that the reflected second beam of electromagnetic radiation is directed to enter said data detector. Steps c. and e. are preferably automated.

The method can be repeated at another location on the sample, especially where the sample is relatively large, (eg. 450 mm square).

The alignment detector substantially centrally located hole can have a shape such as circular, square, rectangular, oval, ellipsoidal, and slit, or any functional shape.

A method of processing electromagnetic beams to eliminate a radially outer annulus thereof comprises placing at least one spatial filter(s) such that said electromagnetic beam passes therethrough, said spatial filter sequentially comprising:
- aperture;
- beam converging at least one lens and/or mirror;
- diaphragm with a pin hole therein located essentially at the focal length of said beam converging at least one lens and/or mirror; and
- beam collimating at least one lens and/or mirror;

such that in use an electromagnetic beam which is caused to pass through said aperture, become focused on and at least partially pass through said pin hole in said diaphragm by said beam converging at least one lens and/or mirror, and become recollimated by said second beam collimating at least one lens and/or mirror before being caused to proceed toward, and interact with, said sample system;

said system being further characterized by a selection from the group consisting of:
- said at least one spatial filter(s) is positioned prior to a beam directing reflective means which directs said electromagnetic beam onto said sample system; and
- there is no beam directing reflective means present prior to said sample system which directs said electromagnetic beam onto said sample system.

Another method of investigating a sample system, in the context of a selection from the group consisting of:
- reflectometer;
- spectrophotometer;
- ellipsometer;
- spectroscopic ellipsometer;
- polarimeter; and
- spectroscopic polarimeter;

which causes a beam of electromagnetic radiation to interact with a sample system;

comprises the steps of:
a. providing a beam of electromagnetic radiation;
b. providing a sample system;
c. placing at least one spatial filter(s) in the pathway of said electromagnetic beam such that said electromagnetic beam at least partially passes therethrough prior to said electromagnetic beam being caused to interact with said sample system; said system being characterized by a selection from the group consisting of:
- said at least one spatial filter(s) is positioned prior to a beam directing reflective means which directs said electromagnetic beam onto said sample system; and
- there is no beam directing reflective means present prior to said sample system which directs said electromagnetic beam onto said sample system; the purpose being to eliminate a radially outer annulus of said electromagnetic beam which is comprised of a low intensity level irregular content.

Said methodology for eliminating a radially outer annulus of said electromagnetic beam can be applied in the systems described herein.

The disclosed invention will be better understood by reference to the Detailed Description Section of this Specification, in coordination with the Drawings.

SUMMARY OF THE INVENTION

A primary purpose and/or objective of the disclosed invention is to present improvements to ellipsometers, polarimeters, spectrophotometers, scatterometers and the like.

A specific purpose and/or objective of the disclosed invention is to present improvements to monochrometers.

Another specific purpose and/or objective of the disclosed invention is to present new alignment detectors and methods of use for aligning samples and angles of incidence.

Another specific purpose and/or objective yet of the disclosed invention is to present multiple use of multiple detector systems.

Yet another specific purpose and/or objective yet of the disclosed invention is to present description of a method of taking data both during and after an evacuation or purging of an enclosed volume.

Other purposes and/or objectives of the disclosed invention will become apparent upon a reading of the Specification and Claims.

DETAILED DESCRIPTION

Figure 1A:
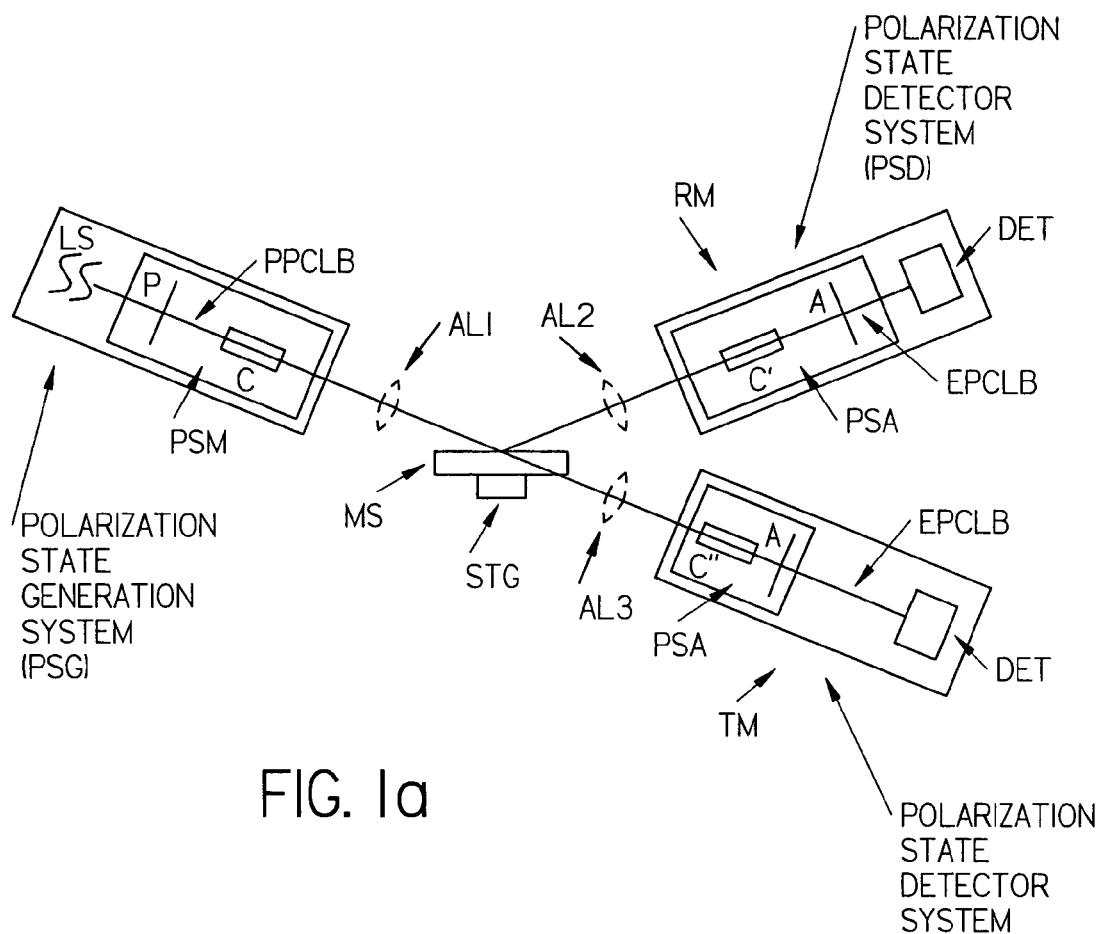
FIG. 1a shows a diagram of an ellipsometer system with both reflection and transmission detectors.

Turning to the Drawings, FIG. 1a shows a diagram of an ellipsometer/polarimeter system for use in both reflection (RF) and transmission (TM) modes. A source of monochromatic or polychromatic electromagnetic radiation (LS) is shown to, via polarization state modifier (PSM), which is demonstrated as being comprised of an Polarizer (P) and optionally a Compensator (C), provide a polarized beam of electromagnetic radiation (PPCLB) which is directed to interact with a material system (MS) which is placed on a stage (STG). (Note that conventional terminology identifies a Polarization State Generation System (PSG) as a combination of said source of monochromatic or polychromatic electromagnetic radiation (LS) and a Polarization State Modifier (PSM), which Polarization State Modifier (PSM) is demonstrated as being comprised of a Polarizer (P) and optionally a Compensator (C)). After interaction with the material system (MS), propagated electromagnetic beam (PPCLB) emerges as (EPCLB), after passing through a polarization state analyzer (PSA) and enters a detector system (DET). (Note that conventional terminology provides that for each of the Reflection (RM) and Transmission (TM) Modes, a Polarization State Analyzer (PSA) is demonstrated as being comprised of an Analyzer (A) and optionally a Compensator (C') or (C") respectively, and that when said Polarization State Analyzer (PSA) is combined with a Detector System (DET), there is formed a Reflection or Transmission Mode Polarization State Detector System (PSD), respectively). It is also to be understood that if the Polarization State Modifier (PSM), and Polarization State Analyzer (PSA) are not present, then FIG. 1a demonstrates a Spectrophotometer system comprised of (LS), (STG/(MS) and (DET). It is to be understood that the angle of incidence of the electromagnetic beam (PPCLB) is often oriented closer to normal to the material sample (MS) upper surface, when the system is operated as a Spectrophotometer. With regard to the present invention, it is to be appreciated that the Detector System(s) (DET) indicated are multiple detector systems mounted on a positionable means (eg. a movable arm), thereby allowing easy alternate positioning of the Detector Systems in at least two locations. Note that such a rotation would be in a vertically oriented plane, as shown in FIG. 1a, but that this is only demonstrative and in any embodiment of the present invention multiple detector system, motion in any plane is within the scope of the Claims, (eg. see FIGS. 8a and 8b). In addition, it is noted that variously shaped apertures and/or focusing lenses (AL1) (AL2) (AL3), preferably achromatic, can be present before and/or after a sample as can functional equivalents to the polarizer/compensator/analyzer combinations.

Figure 1B:
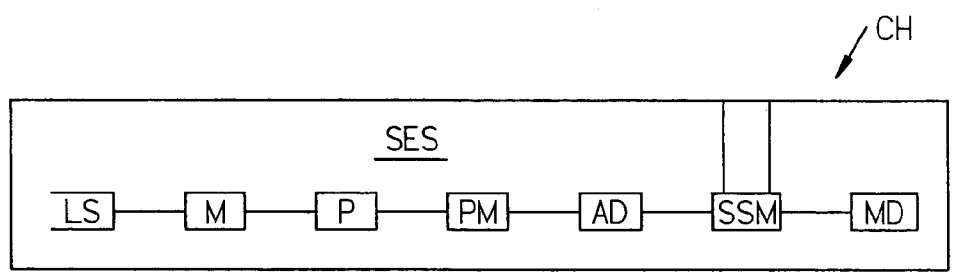
FIG. 1b shows a chamber (CH) which contains an essentially enclosed space (SES), with functional blocks corresponding to VUV-VASE components therewithin.

There is shown in FIG. 1b a chamber (CH) which contains an substantially enclosed space (SES). Within said substantially enclosed space (SES) are shown functional blocks corresponding to Vacuum-Ultra-Violet Variable Angle Spectroscopic Ellipsometer (VUV-VASE) components. In particular, in said substantially enclosed space (SES) there is sequentially shown a source of polychromatic electromagnetic radiation (LS), a Monochromator (M), a polarization state setting means for setting a polarization state in at least a selected small range of wavelengths in a beam including ultraviolet wavelength range electromagnetic radiation (P); a means which enables sequentially modifying a polarization state set by said polarization state setting means, through a plurality of polarization states (PM); an alignment detector means (AD) which can comprise a plurality of detector elements surrounding a substantially centrally located hole through which a beam of electromagnetic radiation can pass, said substantially centrally located hole having a diameter sufficiently large such that about ten (10) times more electromagnetic radiation intensity passes therethrough than does through a 1.27 mm diameter hole, (eg. 2-4 mm diameter), a indication of a subspace sequestering means (SSM) comprising means for placing and maintaining a sample system in a desired position and orientation in a subspace sequestering means, (see specifically the Stage (STG) in FIG. 7a which is in a Sequestered Subspace (SEQS) of the Substantially Enclosed Space (SES)); and a multiple detector system (MD).

It should be appreciated that while the Monochromator (M) is shown in a specific position in FIG. 1b, but except for the source of electromagnetic radiation which must, of course be prior to the sample, can be moved to other locations in the system and be functional. Further, where Infrared wavelengths are desired, the source of polychromatic electromagnetic radiation (LS) and the Monochromator system can be replaced by an Infrared Fourier Transform (IR-FTIR) source system.

Figure 2A:
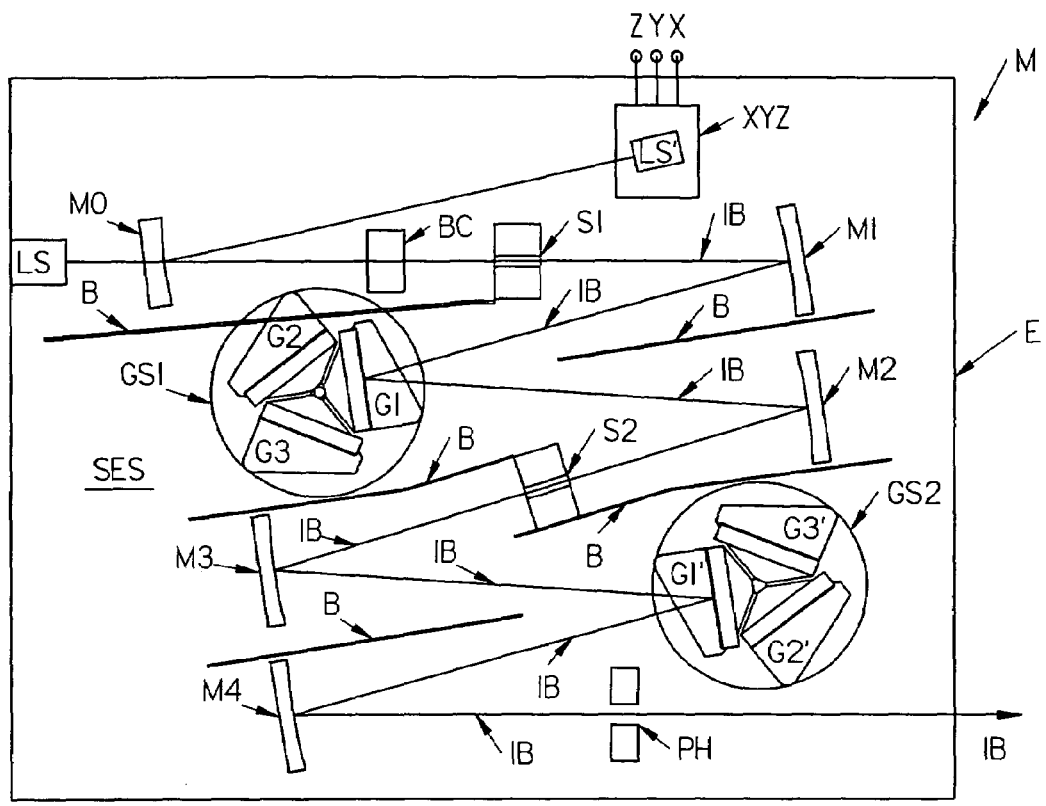
FIG. 2a shows components of a monochromator (M).
Figure 3:
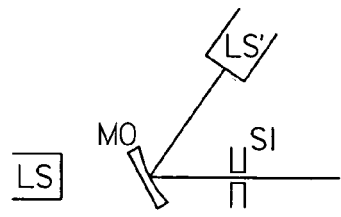
FIG. 3 shows one light source (LS) configuration in the monochromator of FIG. 2.
Figure 4:
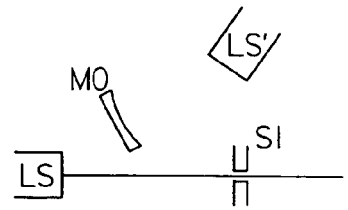
FIG. 4 shows a second light source (LS) configuration in the monochromator of FIG. 2.

FIG. 2a shows the monochromator system (M) in FIG. 1b, in more detail. Shown are an "X" "Y" "Z" positionable source of polychromatic electromagnetic radiation (LS') and a beam directing spherical mirror (M0), a first slit (S1), a second source of a beam (LS), a first spherical mirror (M1), a first grating system (GS1) comprising three gratings (G1) (G2) and (G3), a second spherical mirror (M2), a second slit (S2), a third spherical mirror (M3), a second grating system (GS2) comprising three gratings (G1') (G2') and (G3'), a forth spherical mirror (M4) and a pinhole (PH). FIG. 3 shows the combined source of polychromatic electromagnetic radiation (LS') and a beam directing spherical mirror (M0) in contrast with a second system comprising a source of polychromatic electromagnetic radiation (LS) oriented so that no beam directing spherical mirror (M0) is required. In use the beam directing spherical mirror (M0) can be entered and removed to allow polychromatic electromagnetic radiation to be provided by either (LS) or (LS'). This can be of benefit where, for instance, (LS') is a Xenon lamp; and (LS) is a Deuterium lamp to enable providing wavelengths between approximately 135 nm to 190 nm, and from 190 nm up to 2000 nm or longer. FIG. 4 shows application of a Xenon Lamp (LS) oriented to direct a beam toward the Slit (S1). FIG. 2a also shows the path of a beam (IB) and electromagnetic radiation blocking baffles (B) and a chopper (BC), (which can be placed in any location in beam (IB)).

Figure 2B:
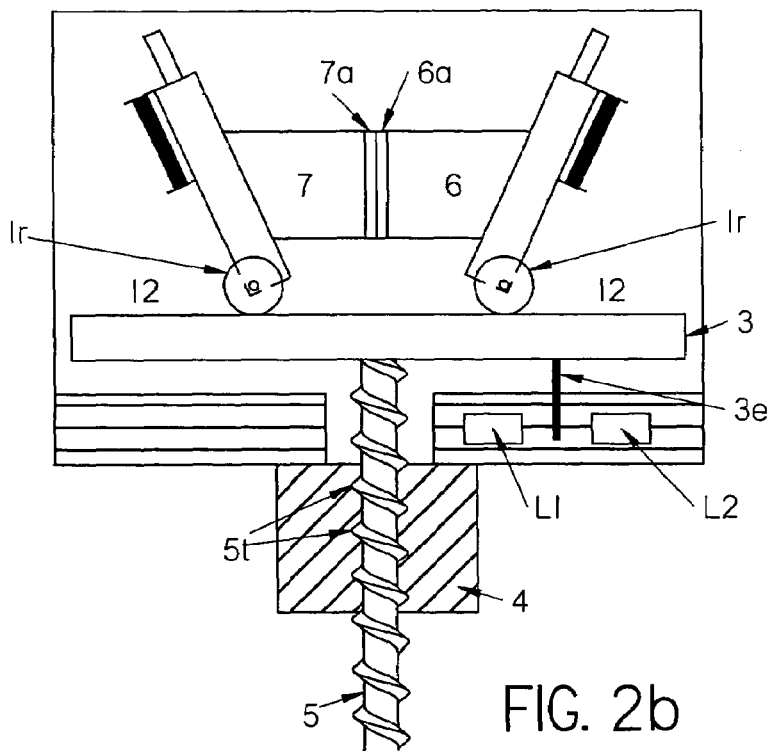
FIG. 2b shows a bi-lateral slit effecting mechanism in the monochromator (M) of FIG. 2.

FIG. 2b shows a bi-lateral slit effecting mechanism which is the preferred mechanism for effecting slit (S1) and (S2) shown in FIG. 2a. Indicated are stage (3) driving screwthread (5t) and hole (4) and knife-blade (6)/(6a) (7)/(7a) roller (1r) means which ride on stage (3) surface (12) so that when stage (3) moves vertically, the knife-blades (6a) (7a) move horizontally apart. Detector means (L1) (L2) and (3e) detecting stage (3) motion.

Figure 2C:
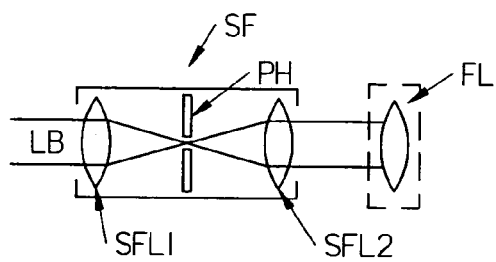
FIGS. 2c, 2d and 2e show Spatial Filtering means.
Figure 2D:
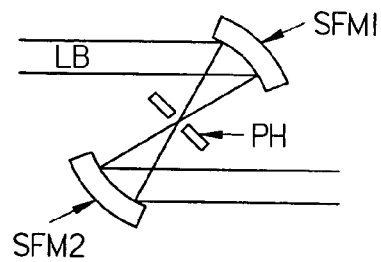
Figure 2E:
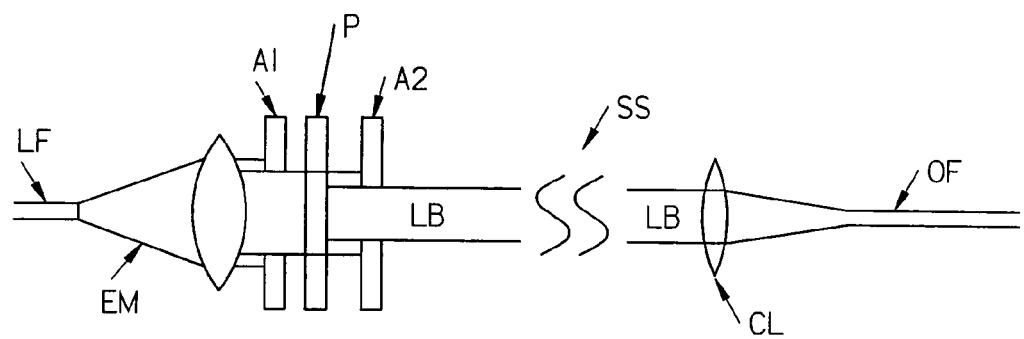

It is also noted that, as described in U.S. Pat. No. 6,456,376 B1, at least one Spatial Filter can be placed into the system. FIGS. 2c and 2d show embodiments of Spatial Filters. Note in FIG. 2c that a collimated beam (LB) is focused onto a Pin Hole (PH) by Lens (SFL1), passes through said Pin Hole (PH) and is recollimated by Lens (SFL2). FIG. 2d shows that the Lenses can be replaced by reflective reflectors (SFM1) and (SFM2). FIG. 2e demonstrates that a Spatial Filter Equivalent can be constructed by focusing an electromagnetic beam (LB), which has been passed through an Aperture (A2) after being collimated by collimating means (L1) and prior to interacting with a sample (SS), onto a Fiber Optic (OF) after interacting with said Sample System (SS), with a converging means (CL). The purpose of the Spatial Filter, (to be read to include the Equivalent shown in FIG. 2e), is to remove an outer annulus region of a beam as its viewed in cross-section. A system as in FIG. 1a can include a Spatial Filter anywhere therewithin, said Spatial Filter being described as comprising:

a. a Source of a beam electromagnetic radiation (LS);
    b. a Polarizer element (P);
    c. optionally a compensator element;
    d. optional additional element(s);
    e. a Stage (STG) for supporting a material system (SS);
    f. optional additional element(s);
    g. optionally a compensator element;
    h. an Analyzer element (A); and
    i. a Data Detector System (MD).

Said spatial filter is present between said Source of a beam electromagnetic radiation (LS) and said Data Detector (MD) and comprises:
    optional aperture;
    beam converging at least one lens and/or mirror;
    diaphragm with a pin hole therein located essentially at the focal length of said beam converging at least one lens and/or mirror; and
    beam collimating at least one lens and/or mirror;

or comprises:
    before a sample an aperture through which a collimated electromagnetic beam is caused to pass; and
    after said sample a converging lens and an optical fiber onto an end of which the converged electromagnetic beam is focused.

Figure 5:
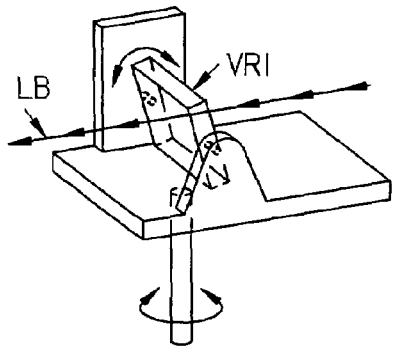
FIG. 5 shows a means which enables sequentially modifying a polarization state set by said polarization state setting means.

FIG. 5 shows the means which enables sequentially modifying a polarization state set by said polarization state setting means, through a plurality of polarization states (MP) can comprise a Berek-type Variable Retarder (VR1) mounted to allow rotation about two axes (S1) and (S2) as a beam of electromagnetic radiation (LB) is caused to pass therethrough.

Figure 6A:
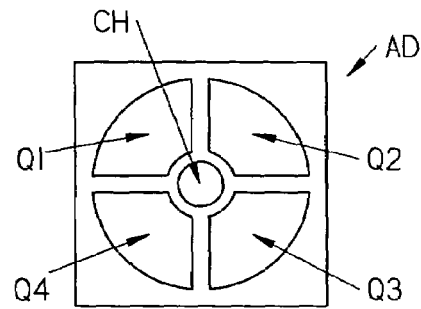
FIG. 6a shows an alignment detector means.

FIG. 6a shows an alignment detector means (AD) comprising a plurality of detector elements, (eg. (Q1), (Q2), (Q3) and (Q4), surrounding a substantially centrally located hole (CG) through which a beam of electromagnetic radiation can pass. In one version of the presently disclosed invention said substantially centrally located hole has a diameter of between 2-4 mm inclusive, which is sufficiently large such that about ten (10) times more intensity passes therethrough than passes through a 1.27 mm diameter hole. Where the hole is present a beam can be passed therethrough perpendicularly toward the surface of a sample system and alignment of said surface to be substantially perpendicular to the locus of said beam then enables directly setting an oblique angle of incidence of said beam to said surface by a definite number of degrees away from said normal. It is noted that the alignment detector substantially centrally located hole (CH) can have a shape such as circular, square, rectangular, oval, ellipsoidal, and slit, or any functional shape.

In another version of the presently disclosed invention there need not be any central hole at all because the alignment detector is positioned to intercept a beam which reflects from the surface of a sample system obliquely. This version requires calibration of the oblique angle so that when the surface of the sample is rotated to effect an oblique angle of incidence of the beam thereto, it is accounted for as an initial offset. The positioning of the alignment detector then requires an additional step to calibrate the initial angle of incidence of the beam to the sample system surface, but in return for the additional required calibration, the beam does not have to pass through a hole and no intensity at all is lost as a result.

Figure 6B:
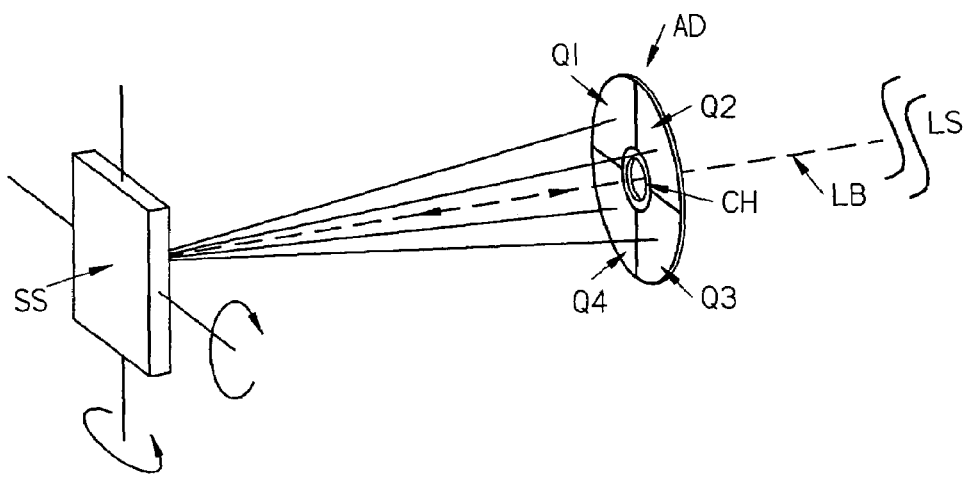
FIG. 6b shows a source of electromagnetic radiation (LS), an Alignment Detector (AD) and a Sample System (SS).
Figure 6C:
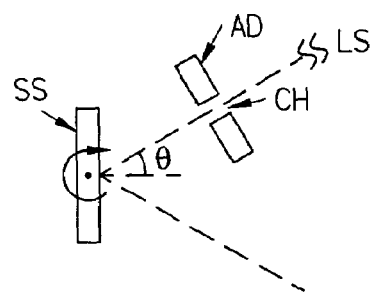
FIG. 6c shows that once the beam of electromagnetic radiation (LB) from the source of electromagnetic radiation (LS) has been so to approach the Sample System (SS) along a normal to its surface, the Sample System (SS) can be rotated so that the beam of electromagnetic radiation (LB) approaches the Sample System (SS) along an Angle-of-Incidence ($\Theta$).
Figure 6D:
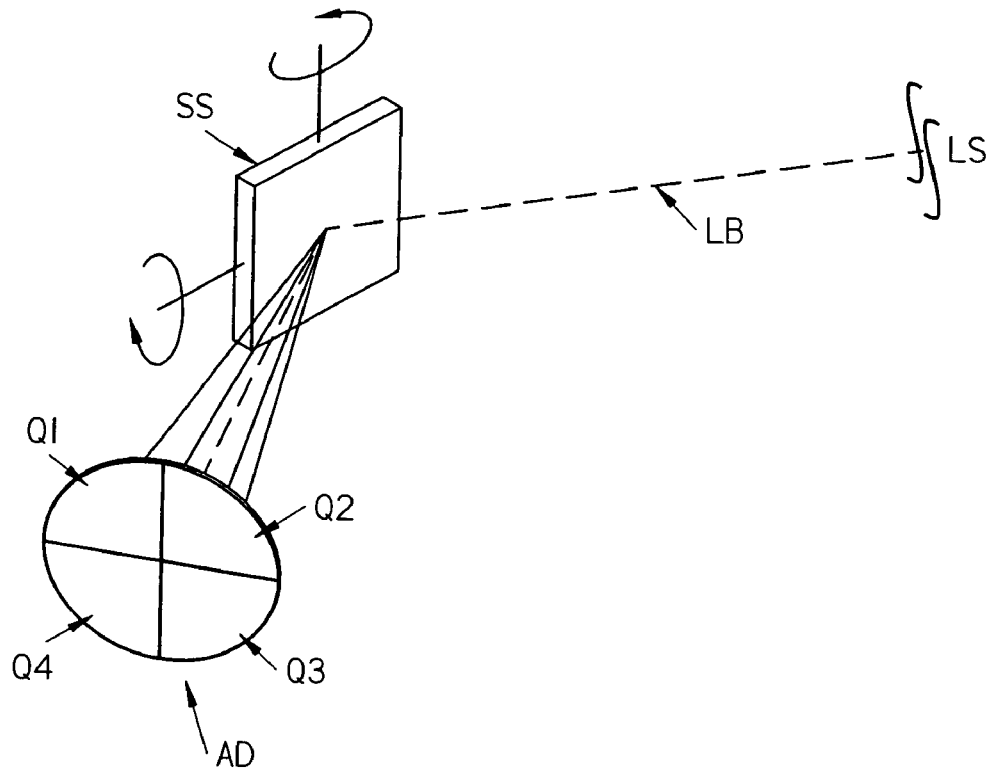
FIG. 6d shows a variation of the FIG. 6b alignment system, wherein the beam of electromagnetic radiation (LB) is caused to approach the surface of the Sample system (SS) and an Angle such that the reflected beam encounters the Alignment Detector (AD).
Figure 6E:
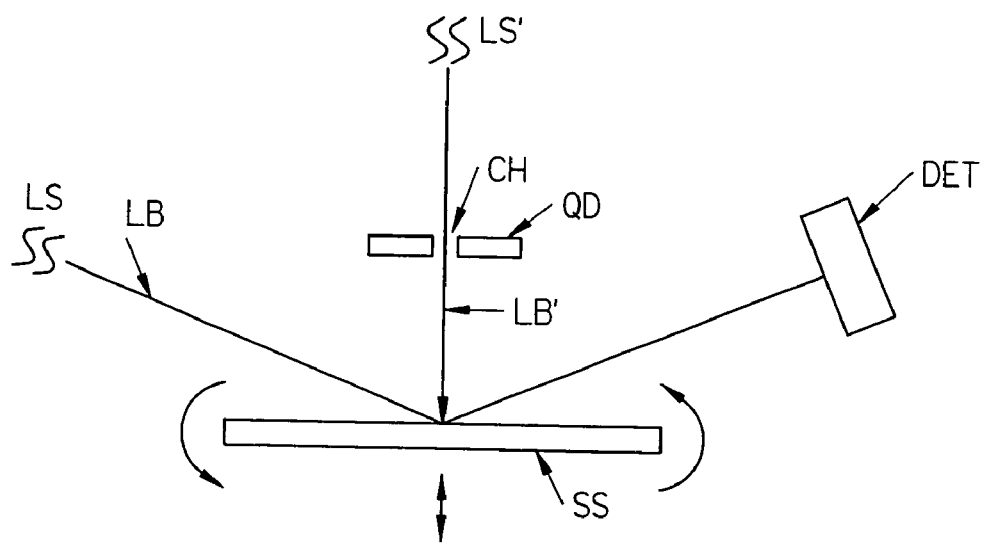
FIG. 6e shows yet another approach to sample system alignment utilizing two beams of electromagnetic radiation.

FIG. 6b shows a source of electromagnetic radiation (LS), an Alignment Detector (AD) and a Sample System (SS). Note that the beam of electromagnetic radiation (LB) from the source of electromagnetic radiation (LS) proceeds through a centrally located hole (CH) in the Alignment Detector (AD) and reflects 180 degrees from the Sample System (SS), which dispersed portions thereof entering the Detector Elements (Q1), (02), (Q3) and (Q4). When the Sample System (SS) is aligned optimally, the signal to each Detector Element (Q1), (Q2), (Q3) and (Q4) will typically be substantially equal. FIG. 6c shows that once the beam of electromagnetic radiation (LB) from the source of electromagnetic radiation (LS) has been so to approach the Sample System (SS) along a normal to its surface, the Sample System (SS) can be rotated so that the beam of electromagnetic radiation (LB) approaches the Sample System (SS) along an Angle-of-Incidence (Θ). FIG. 6d shows a variation of the FIG. 6b alignment system, wherein the beam of electromagnetic radiation (LB) is caused to approach the surface of the Sample system (SS) and an Angle such that the reflected beam encounters the Alignment Detector (AD). Again, the Sample system (SS) is aligned so that the dispersed beam enters the Detector Elements (Q1), (Q2), (Q3) and (Q4) at approximately equal intensities. And again, once the Sample System (SS) is so aligned, it can be rotated an additional angle to provide that the beam of electromagnetic radiation (LB) approaches the surface of the Sample System (SS) at an intended Angle-of-Incidence. In this case, an additional Calibration is necessary to precisely determine the Angle-of-Incidence at which the beam of electromagnetic radiation (LB) approaches the surface of the Sample System (SS) during Alignment, and that must be factored into the rotation effected to position the Sample System (SS) at an Angle-of-Incidence appropriate for taking Data. FIG. 6e shows yet another approach of aligning a Sample System (SS). An electromagnetic beam (LB') is focused on aligning a stage/sample (SS), (eg. a large area flat panel for instance), with respect to said a beam of electromagnetic radiation (LS'), but utilizes two beams (LS) (LS) of electromagnetic radiation. A Multi-element, (eg. Quad-Detector (OD)), sensor system again allows for entering a first beam (LS') of electromagnetic radiation through a centrally located opening therein and causes said beam to approach and reflect from the surface of the Sample System (SS). Said method then provides that the stage/sample (S) be then tilted until the first electromagnetic beam (LS') reflects directly back therefrom with dispersion therefrom entering the Multiple Detectors which surround the centrally located opening substantially equally. This determines the orientation of the surface of Sample System (SS) the with respect to said first electromagnetic beam (LS'). The system further provides a source of a second beam (LS) of electromagnetic radiation, (it being oriented with respect to the first beam of electromagnetic radiation in a known calibrated way), from which a second beam (LB) of electromagnetic radiation is caused to approach the surface of the Sample System (S) at an oblique angle, reflect therefrom and proceed generally toward a provided Detector (DET). The method then provides for moving the stage/sample system (SS) along a perpendicular to the surface of the sample until the data detector is found to receive an electromagnetic beam of a maximum intensity.

Figure 7A:
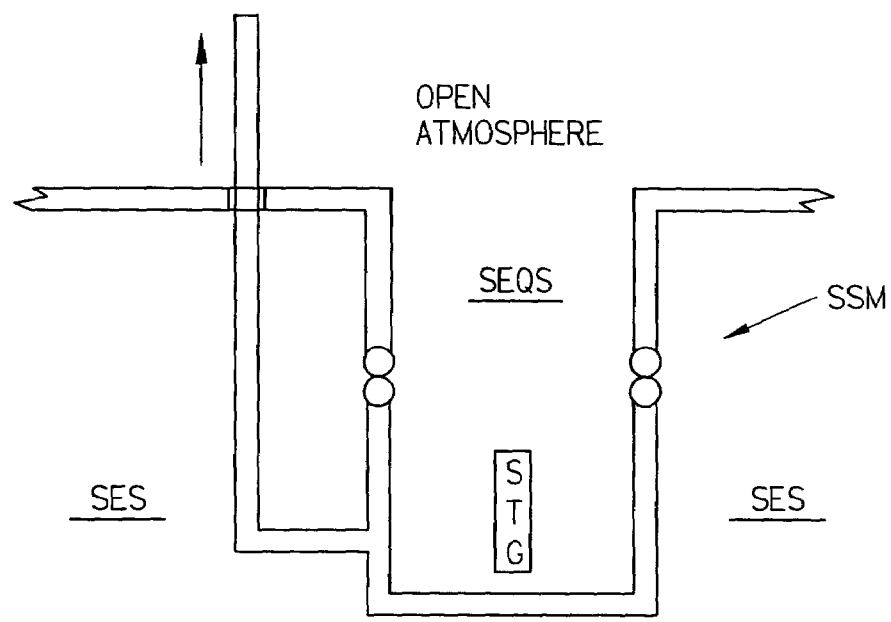
FIG. 7a shows a means for placing and maintaining a sample system in a desired position and orientation (STG), said means for placing and maintaining a sample system in a desired position and orientation being positioned in a sequestered subspace (SEQS) of said substantially enclosed space (SES) which can be sequestered by a subspace sequestering means (SSM).
Figure 7B:
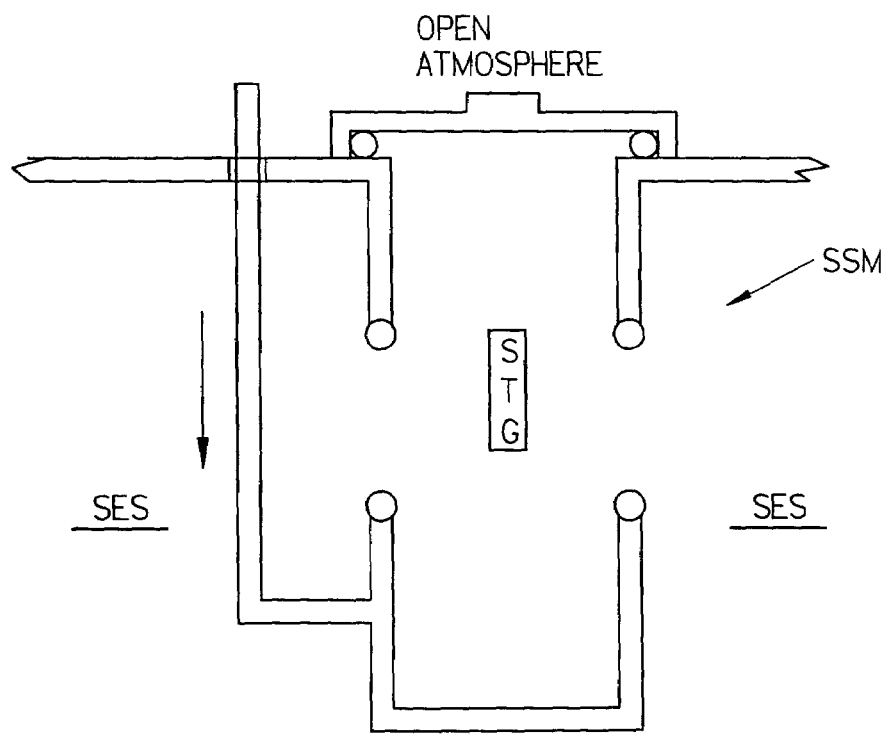
FIG. 7b shows the subspace sequestering means (SSM) of FIG. 7a opening the means for placing and maintaining a sample system in a desired position and orientation (STG) to the substantially enclosed space (SES).
Figure 7C:
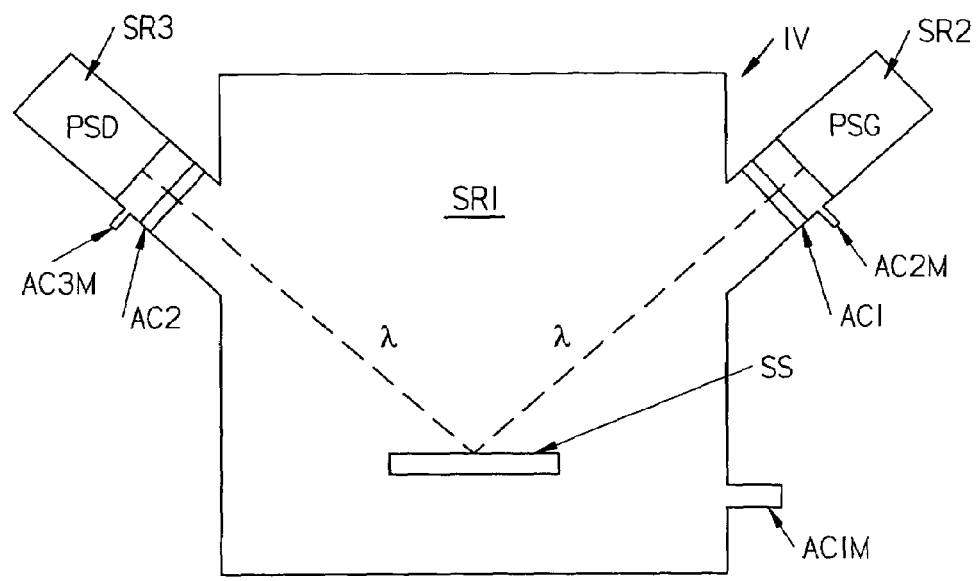
FIG. 7c demonstrates that an environmental control chamber can comprises multiple regions.

FIG. 7a shows a means for placing and maintaining a sample system in a desired position and orientation (STG), said means for placing and maintaining a sample system in a desired position and orientation being positioned in a sequestered subspace (SEQS) of said substantially enclosed space (SES) which can be sequestered by a subspace sequestering means (SSM). FIG. 7b shows the subspace sequestering means (SSM) of FIG. 7a opening the means for placing and maintaining a sample system in a desired position and orientation (STG) to the substantially enclosed space (SES). FIG. 7c demonstrates that an environmental control chamber can comprises multiple regions which can be separately sequestered. Shown are separate regions in which are present a Sample (SS), a Polarization State Generator (PSG) and a Polarization State Detector (PSD). Note that Ambient Control Means (AC1M), (AC2M) and (AC3M) are associated with said sequestered regions ((SR1), (SR2) and (SR3) respectively and allow entry of purging gas or evacuation of their associated sequestered region. Sequestering Means (AC1) and (AC2), (eg. windows), separate the Sequestered Regions (SR2) from (SR1) and (SR1) from (SR3) respectively. The environment in each sequestered region can then be separately controlled. Note that sequestered region (SR1) can represent either (SES) or (SEQS) in FIGS. 7a and 7b.

Figure 8A:
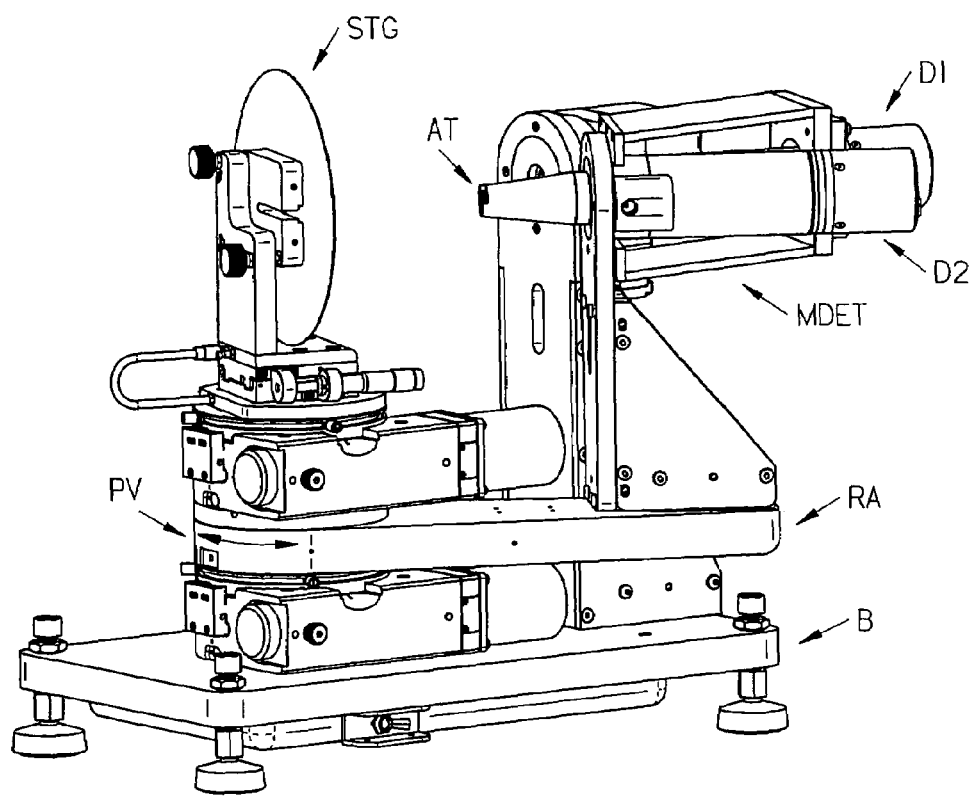
FIGS. 8a and 8b show multiple detector systems (MDET) comprised of at least detectors (D1) and (D2).
Figure 8B:
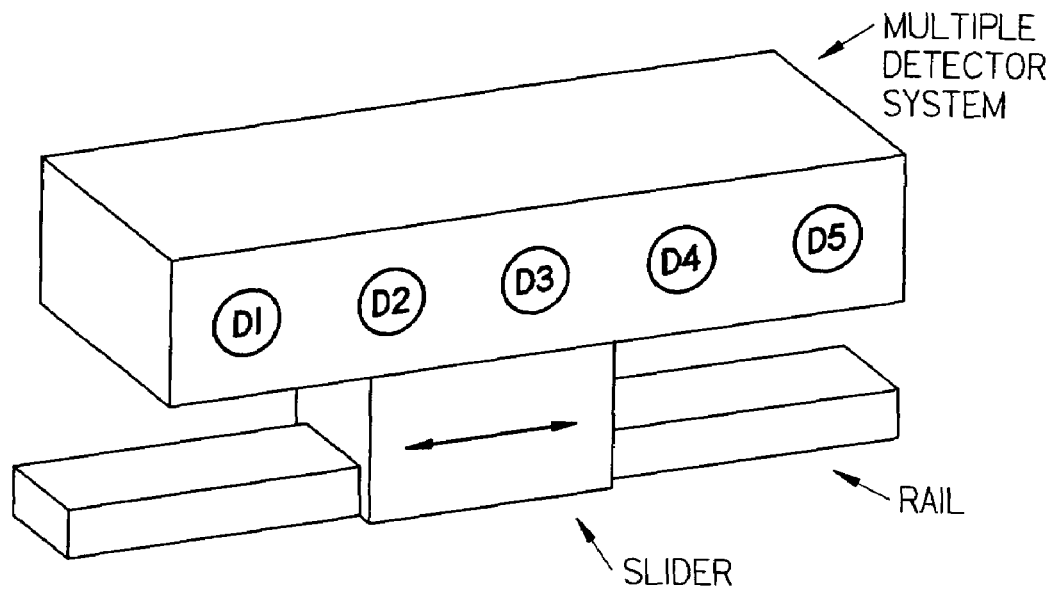
Figure 8C:
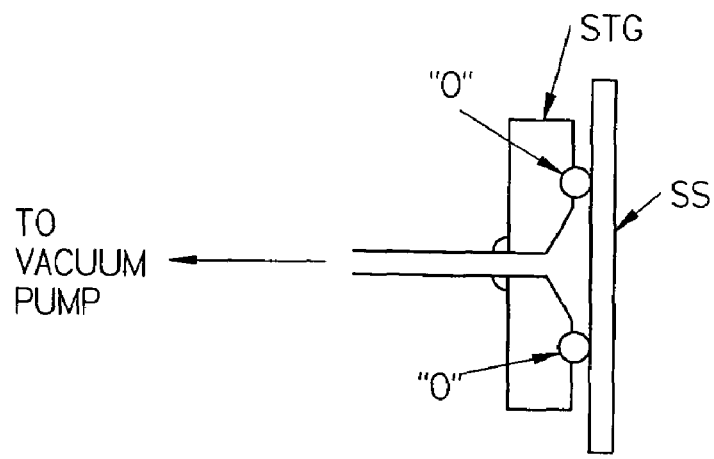
FIG. 8c shows the Sample positioning Stage (STG) can comprise a vacuum chuck.

FIG. 8a shows a multiple detector system (MDET) comprised of detectors (D1) and (D2), each of which can be rotated about pivot (PV) to place it into the path of a beam of electromagnetic radiation, without removing either detector from its attachment to base (B) via pivot (PV). FIG. 8b shows another embodiment of a multiple detector system (MDET). FIG. 8c shows that the Stage (STG) can be a vacuum chuck in which a Sample (SS) is held in place on an "O" Ring via a suction generated by a vacuum pump.

Figure 9:
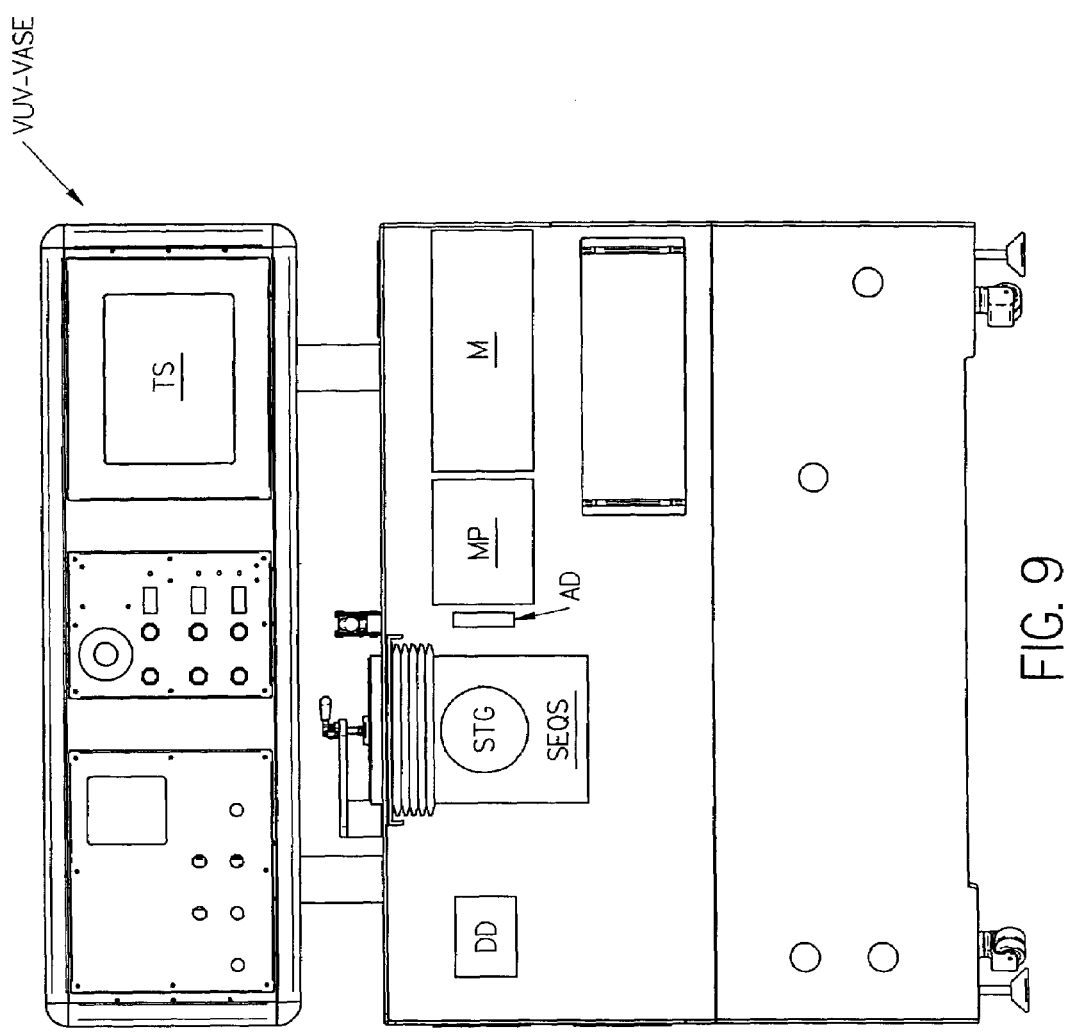
FIG. 9 provides a front elevational view showing the general layout of the J. A. Woollam Co. VUV-VASE.

FIG. 9 provides a front elevational view showing the general layout of the J. A. Woollam Co. VUV-VASE. Note the sequence of the Monochromator (M), means which enables sequentially modifying a polarization state set by said polarization state setting means, through a plurality of polarization states (MP), Alignment Detector, means for placing and maintaining a sample system in a desired position and orientation (STG), said means for placing and maintaining a sample system in a desired position and orientation being positioned in a sequestered subspace (SEQS) of said substantially enclosed space (SES) which can be sequestered by a subspace sequestering means (SSM), and multiple detector system (MDET). Also indicated is a Touch Screen (TS) Control.

It is specifically noted that while not limiting, the Stage (STG) for securing a Sample System can conveniently include a vacuum chuck which allows easily securing and releasing the sample by providing a suction, or not. In addition, the Stage (STG) for securing a Sample System can also contain a heating and/or cooling means for controlling the temperature of a sample.

It is noted that apertures identified in the foregoing can be of any functional shape, such as circular, oval, elliptical, square, rectangular, slit etc. as found to optimize some parameter.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of automatically aligning the surface of a sample system with respect to the locus of an incident beam of electromagnetic radiation comprising the steps of:
   a) providing a system which comprises a source of a beam of electromagnetic radiation and an alignment detector, which alignment detector comprises a plurality of detector elements which are positioned to surround a centrally located hole thereof, which centrally located hole has a diameter sufficiently large such that more intensity of a beam passes therethrough than does through a 1.27 mm diameter hole; said system further comprising computing means to which at least two of said plurality of alignment detector, detector elements are functionally electrically interconnected; said system further comprising a means for supporting and controlling the orientation of the surface of a sample system; said means for supporting and controlling the orientation of the surface of a sample system comprising stepper-motor means which is functionally electrically interconnected to said computing means;
   b) causing said source of a beam of electromagnetic radiation to provide a beam of electromagnetic radiation which is directed to pass through said centrally located hole in said alignment detector, and placing a sample system on said means for supporting and controlling the orientation of the surface of a sample system such that the orientation of the surface of said sample system is approximately perpendicular to the locus of said beam of electromagnetic radiation which is provided by said source of a beam of electromagnetic radiation and passes through said centrally located hole in said alignment detector;
   c) causing said computing means to receive signals from said at least two detector elements of said alignment detector and in response apply signal to said stepper-motor means to the end that said surface of said sample system is caused to be oriented substantially perpendicular to the locus of a beam of electromagnetic radiation which is provided by said source of a beam of electromagnetic radiation and passes through said centrally located hole in said alignment detector;
   d) as necessary repeating step c) to the end that said surface of said sample system is caused to be oriented at least within +/−0.1 degree, perpendicular to the locus of a beam of electromagnetic radiation which is provided by said source of a beam of electromagnetic radiation and passes through said centrally located hole in said alignment detector;
   e) causing said stepper motor means to re-orient the surface of said sample system so that a normal thereto is directed at a selected number of degrees with respect to the orientation of said locus of said beam of electromagnetic radiation which is provided by said source of a beam of electromagnetic radiation and passes through said centrally located hole in said alignment detector;
   such that said beam of electromagnetic radiation approaches said surface of said sample system at a known angle of incidence thereto;
   said chance in orientation of said sample system surface constituting a concrete and tangible change achieved by practice of said method.

2. A method of aligning a sample as in claim 1, wherein the steps c. and e. are automated.

3. A method of aligning a sample as in claim 1, which comprises repeating the method at another location on the sample.

4. A method of aligning the surface of a sample system with respect to the locus of an incident beam of electromagnetic radiation comprising the steps of:
   a) providing a system which comprises a source of a beam of electromagnetic radiation and an alignment detector, which alignment detector comprises a plurality of detector elements, said system further comprising computing means to which at least two of said plurality of alignment detector, detector elements are functionally electrically interconnected, said system further comprising a means for supporting and controlling the orientation of the surface of a sample system; said means for supporting and controlling the orientation of the surface of a sample system comprising stepper-motor means which is functionally electrically interconnected to said computing means;
   b) causing said source of a beam of electromagnetic radiation to provide a beam of electromagnetic radiation which is directed toward said means for supporting and controlling the orientation of the surface of a sample system and placing a sample system on said means for supporting and controlling the orientation of the surface of a sample system such that the orientation of the surface of said sample system is at an oblique angle to the locus of said beam of electromagnetic radiation, such that said beam reflects from said sample system and proceed toward said alignment detector;
   c) causing said computing means to receive signals from said at least two detector elements of said alignment detector and in response apply signal to said stepper-motor means to the end that said surface of said sample system is caused to be oriented such that approximately equal signals are provided by said at least two detector elements of said alignment detector;
   d) as necessary repeating step c to optimize detector element signal equality;
   e) causing said stepper motor means to re-orient the surface of said sample system a selected number of degrees with respect to the orientation of said locus of said beam of electromagnetic radiation which is provided by said source of a beam of electromagnetic radiation;
   such that said beam of electromagnetic radiation approaches said surface of said sample system at a known angle of incidence thereto;
   said change in orientation of said sample system surface constituting a concrete and tangible change achieved by practice of said method.

5. A method of aligning a sample as in claim 4, wherein the steps b. and c. are automated.

6. A method of aligning a sample as in claim 4, which comprises repeating the method at another location on the sample.

7. A method for aligning a sample as in claim 4, in which said sample system is characterized by a selection from the group consisting of:
- being isotropic and non-depolarizing;
- being isotropic and depolarizing;
- being anisotropic and non-depolarizing;
- being anisotropic and depolarizing;

and in which said beam of electromagnetic radiation provided by said source is further characterized by a selection from the group consisting of:
- it comprises a single wavelength;
- it comprises multiple wavelengths;
- it comprises a plurality of scanned wavelengths which are sequentially scanned individually;
- it comprises ultraviolet wavelengths;

and is further characterized by a selection from the group consisting of:
- unpolarized;
- partially polarized;
- randomly polarized;
- linearly polarized;
- with respect to said sample linearly "p" polarized;
- with respect to said sample linearly "s" polarized;
- circularly polarized.

8. A method for aligning a sample system as in claim 4, in which said beam of electromagnetic radiation provided by said source is characterized by a selection from the group consisting of being:
- non-polarized before and after said sample;
- non-polarized before said sample, and polarized after interaction with said sample;
- polarized before and after said sample.

9. A method of aligning a sample as in claim 4, in which the provided system further comprises means for effecting modulation of said beam of electromagnetic radiation said modulation being of at least one selection from the group consisting of:
- Electromagnetic Beam Magnetic "B" Field;
- Electromagnetic Beam Electric "E" Field;
- Electromagnetic Beam Flux "$E^2$";
- Ambient Environment Composition, (eg. liquid, gas);
- Sample System Temperature, (which can be above or below room temperature);
- Sample System Strain;
- Pressure applied to Sample System.

* * * * *